(12) United States Patent
Jiang et al.

(10) Patent No.: US 12,291,652 B2
(45) Date of Patent: May 6, 2025

(54) ZWITTERIONIC DOUBLE NETWORK HYDROGELS

(71) Applicant: University of Washington, Seattle, WA (US)

(72) Inventors: Shaoyi Jiang, Seattle, WA (US);
Hsiang-Chieh Hung, Seattle, WA (US);
Dianyu Dong, Seattle, WA (US);
Caroline Tsao, Seattle, WA (US);
Chenjue Tang, Seattle, WA (US); Joel MacArthur, Seattle, WA (US)

(73) Assignee: University of Washington, Seattle, WA (US)

( * ) Notice: Subject to any disclaimer, the term of this patent is extended or adjusted under 35 U.S.C. 154(b) by 803 days.

(21) Appl. No.: 17/268,310

(22) PCT Filed: Aug. 14, 2019

(86) PCT No.: PCT/US2019/046558
§ 371 (c)(1),
(2) Date: Feb. 12, 2021

(87) PCT Pub. No.: WO2020/106338
PCT Pub. Date: May 28, 2020

(65) Prior Publication Data
US 2021/0171783 A1 Jun. 10, 2021

Related U.S. Application Data

(60) Provisional application No. 62/818,574, filed on Mar. 14, 2019, provisional application No. 62/718,759, filed on Aug. 14, 2018.

(51) Int. Cl.
| | |
|---|---|
| *C09D 5/16* | (2006.01) |
| *A61L 24/00* | (2006.01) |
| *A61L 27/34* | (2006.01) |
| *A61L 27/52* | (2006.01) |
| *A61L 29/08* | (2006.01) |
| *A61L 29/14* | (2006.01) |
| *A61L 31/10* | (2006.01) |
| *A61L 31/14* | (2006.01) |
| *C08F 267/10* | (2006.01) |
| *C08J 3/075* | (2006.01) |
| *C08J 3/24* | (2006.01) |
| *C08L 51/00* | (2006.01) |
| *C09D 151/00* | (2006.01) |

(52) U.S. Cl.
CPC ........ *C09D 5/1662* (2013.01); *A61L 24/0031* (2013.01); *A61L 27/34* (2013.01); *A61L 27/52* (2013.01); *A61L 29/085* (2013.01); *A61L 29/145* (2013.01); *A61L 31/10* (2013.01); *A61L 31/145* (2013.01); *C08F 267/10* (2013.01); *C08J 3/075* (2013.01); *C08J 3/246* (2013.01); *C08L 51/003* (2013.01); *C09D 5/1637* (2013.01); *C09D 151/003* (2013.01); *C08J 2300/208* (2013.01); *C08J 2333/14* (2013.01); *C08J 2333/22* (2013.01); *C08J 2333/24* (2013.01); *C08J 2381/10* (2013.01); *C08J 2433/14* (2013.01); *C08J 2433/22* (2013.01); *C08J 2433/24* (2013.01); *C08J 2477/00* (2013.01)

(58) Field of Classification Search
CPC ........ A61L 27/34; A61L 27/52; A61L 29/085; A61L 29/145; A61L 31/10; A61L 31/145; A61L 24/0031; C08F 267/10; C08J 3/075; C08J 3/246; C08J 2300/208; C08J 2381/10; C08J 2477/00; C08J 2333/14; C08J 2333/22; C08J 2333/24; C08J 2433/14; C08J 2433/22; C08J 2433/24; C08L 51/003; C09D 5/1662; C09D 5/1637; C09D 151/003
See application file for complete search history.

(56) References Cited

U.S. PATENT DOCUMENTS

| | | | |
|---|---|---|---|
| 7,879,444 B2 | 2/2011 | Jiang et al. | |
| 8,828,434 B2 | 9/2014 | Su et al. | |
| 9,738,780 B2 | 8/2017 | Jiang et al. | |
| 2015/0197644 A1 | 7/2015 | Chang et al. | |
| 2015/0335790 A1 | 11/2015 | Song et al. | |
| 2017/0028103 A1 | 2/2017 | Song et al. | |
| 2017/0209625 A1 | 7/2017 | Song et al. | |
| 2017/0226339 A1 | 8/2017 | Zhao et al. | |
| 2017/0266350 A1 | 9/2017 | Jiang et al. | |

FOREIGN PATENT DOCUMENTS

| | | |
|---|---|---|
| CN | 105233709 A | 1/2016 |
| CN | 108727937 A | 11/2018 |
| WO | 2017218507 A1 | 12/2017 |
| WO | 2018152395 A1 | 8/2018 |

OTHER PUBLICATIONS

Office Action mailed Nov. 9, 2022, issued in corresponding Chinese Application No. 2019800654815, 10 pages.
Second Chinese Office Action mailed Jul. 29, 2023, issued in corresponding Chinese Application No. 201980065481.5, 11 pages.
(Continued)

*Primary Examiner* — Patrick D Niland
(74) *Attorney, Agent, or Firm* — Christensen O'Connor Johnson Kindness PLLC

(57) ABSTRACT

Zwitterionic double network hydrogels, methods for making zwitterionic double network hydrogels, methods for using zwitterionic double network hydrogels, and articles made from and coated with zwitterionic double network hydrogels.

37 Claims, 21 Drawing Sheets

(56) References Cited

OTHER PUBLICATIONS

Bai, T., et al., "Zwitterionic fusion in hydrogels and spontaneous and time-independent self-healing under physiological conditions", Biomaterials 35 (2014) 3926-3933.

Chang, Y. et al., "Tunable Bioadhesive Copolymer Hydrogels of Thermoresponsive Poly(N-isopropyl acrylamide) Containing Zwitterionic Polysulfobetaine", Biomacromolecules 2010, 11, 4, 1101-1110.

Chen, H. et al., "Molecular Understanding and Structural-Based Design of Polyacrylamides and Polyacrylates as Antifouling Materials", Langmuir, Mar. 17, 2016, 32, 14, 3315-3330.

Chou, Y.N et al., "Ultra-low fouling and high antibody loading zwitterionic hydrogel coatings for sensing and detection In complex media", Acta Biomaterialia, 40 (2016) 31-37.

He, Y. et al., "Improved Mechanical Properties of Zwitterionic Hydrogels with Hydroxyl Groups", J. Phys. Chem. B, 2012, 116, 19, 5766-5770.

He, H. et al., "Simple Thermal Pretreatment Strategy to Tune Mechanical and Antifouling Properties of Zwitterionic Hydrogels", Langmuir, 2019, 35, 5, 1828-1836.

Sun, D. et al., "Effect of water content on microstructures and oxygen permeation in PSiMA-IPN-PMPC hydrogel: a molecular simulation study", Chemical Engineering Science, 78 (2012) 236-245.

Tai, F.I., et al., "Interaction Forces on Polyampholytic Hydrogel Gradient Surfaces", ACS Omega, Mar. 21, 2019, 4, 3, 5670-5681.

Bai, T., et al., "Construction of an ultrahigh strength hydrogel with excellent fatigue resistance based on strong dipole-dipole interaction", Soft Matter, 2011, 7, 2825.

Venault, A., et al., "Hemocompatible biomaterials of zwitterionic sulfobetaine hydrogels regulated with pH-responsive DMAEMA random sequences", International journal of polymeric materials, vol. 65, No. 2, 2016, 65-74.

Wang, J., et al., "Ionic starch-based hydrogels for the prevention of nonspecific protein adsorption", Carbohydrate Polymers 117 (2015) 384-391.

Xiao, S., et al., "Salt-Responsive Bilayer Hydrogels with Pseudo-Double-Network Structure Actuated by Polyelectrolyte and Antipolyelectrolyte Effects", ACS Appl. Mater. Interfaces 2017, 9, 24, 20843-20851.

Yin, H., et al., "Double network hydrogels from polyzwitterions: high mechanical strength and excellent anti-biofouling properties", J. Mater. Chem. B, 2013, 1, 3685.

Zhang, Z., et al., "Physical, Chemical, and Chemical-Physical Double Network of Zwitterionic Hydrogels", J. Phys. Chem. B 2008, 112, 5327-5332.

Zhang, H. et al., "In Situ Gelable Interpenetrating Double Network Hydrogel Formulated from Binary Components: Thiolated Chitosan and Oxidized Dextran", Biomacromolecules 2011, 12, 5, 1428-1437.

International Search Report mailed May 8, 2020, issued in corresponding International Application No. PCT/US2019/46558, filed Aug. 14, 2019, 4 pages.

Written Opinion of the International Searching Authority mailed May 8, 2020, issued in corresponding International Application No. PCT/US2019/46558, filed Aug. 14, 2019, 15 pages.

Fourth Office Action mailed Apr. 8, 2024, issued in corresponding Chinese Application No. 2019800654815, 9 pages.

ZWITTERIONIC DOUBLE NETWORK HYDROGELS

CROSS-REFERENCES TO RELATED APPLICATIONS

This application is a US national stage application based on PCT/US2019/046558, filed Aug. 14, 2019, which claims the benefit of U.S. Application No. 62/718,759, filed Aug. 14, 2018, and U.S. Application No. 62/818,574, filed Mar. 14, 2019, each of which is expressly incorporated herein by reference in its entirety.

STATEMENT OF GOVERNMENT LICENSE RIGHTS

This invention was made with government support under Grant Nos. N00014-16-1-3084 and N00014-19-1-2063 awarded by the Office of Naval Research. The government has certain rights in the invention.

BACKGROUND OF THE INVENTION

Hydrogels with three-dimensional crosslinked networks and high capacity of water are of interest because of their potential in biomedical applications, such as biosensor devices, tissue implants, and contact lenses or marine applications, such as ship hulls, marine structures, marine sensors and fishing nets. Hydrogels made from zwitterionic materials are further of high interest for their superhydrophilicity and excellent non-fouling properties that prevent complications and device failure by resisting nonspecific biofouling from proteins, cells, and micro-organisms. However, due to their polyelectrolyte nature and high glass transition temperature (Tg), improvement in mechanical properties of zwitterionic hydrogels is desirable.

Despite the advantageous nonfouling properties of zwitterionic hydrogels, a need exists for zwitterionic hydrogels having improved mechanical properties. The present invention seeks to fulfill this need and provides further related advantages.

SUMMARY OF THE INVENTION

The present invention provides zwitterionic double network hydrogels, methods for making zwitterionic double network hydrogels, methods for using zwitterionic double network hydrogels, and articles made from and coated with zwitterionic double network hydrogels.

In one aspect, the invention provides zwitterionic double network hydrogels.

In one embodiment, the zwitterionic double network hydrogel is a double network hydrogel, comprising:
(a) a first polymeric network comprising a first crosslinked zwitterionic polymer having from about 50 to about 100 mole percent zwitterionic moieties; and
(b) a second polymeric network comprising a second crosslinked zwitterionic polymer having from about 50 to about 100 mole percent zwitterionic moieties, wherein the double network hydrogel has a compressive fracture stress of greater than about 0.9 MPa.

In another embodiment, the zwitterionic double network hydrogel is a double network hydrogel, comprising:
(a) a first chemical polymeric network comprising a first crosslinked zwitterionic polymer having from about 50 to about 100 mole percent zwitterionic moieties; and
(b) a second chemical polymeric network comprising a second zwitterionic polymer having from about 50 to about 100 mole percent zwitterionic moieties.

In a further embodiment, the zwitterionic double network hydrogel is a double network hydrogel, comprising:
(a) a first polymeric network comprising a first crosslinked zwitterionic polymer having from about 50 to about 100 mole percent zwitterionic moieties, wherein the first crosslinked zwitterionic polymer is not a poly(sulfobetaine); and
(b) a second polymeric network comprising a second crosslinked zwitterionic polymer having from about 50 to about 100 mole percent zwitterionic moieties.

In another embodiment, the zwitterionic double network hydrogel is a double network hydrogel, comprising:
(a) a first polymeric network comprising a first crosslinked polymer, wherein the first polymeric network is a hydrogel; and
(b) a second polymeric network comprising a second crosslinked zwitterionic polymer having from about 50 to about 100 mole percent zwitterionic moieties.

In a further embodiment, the zwitterionic double network hydrogel is a double network hydrogel, comprising:
(a) a first polymeric network comprising a first crosslinked polymer, wherein the first polymeric network is a hydrogel; and
(b) a second polymeric network comprising a crosslinked poly(sulfobetaine) having from about 50 to about 100 mole percent zwitterionic moieties, wherein the double network hydrogel has a compressive fracture stress of greater than about 0.9 MPa.

In another aspect, the invention provides methods for making the zwitterionic double network hydrogels. In one embodiment, the method is a two-step method. In another embodiment, the method is a one-step (single-pot) process.

In a further aspect of the invention, articles of manufacture made from or that include the zwitterionic double network hydrogel are provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
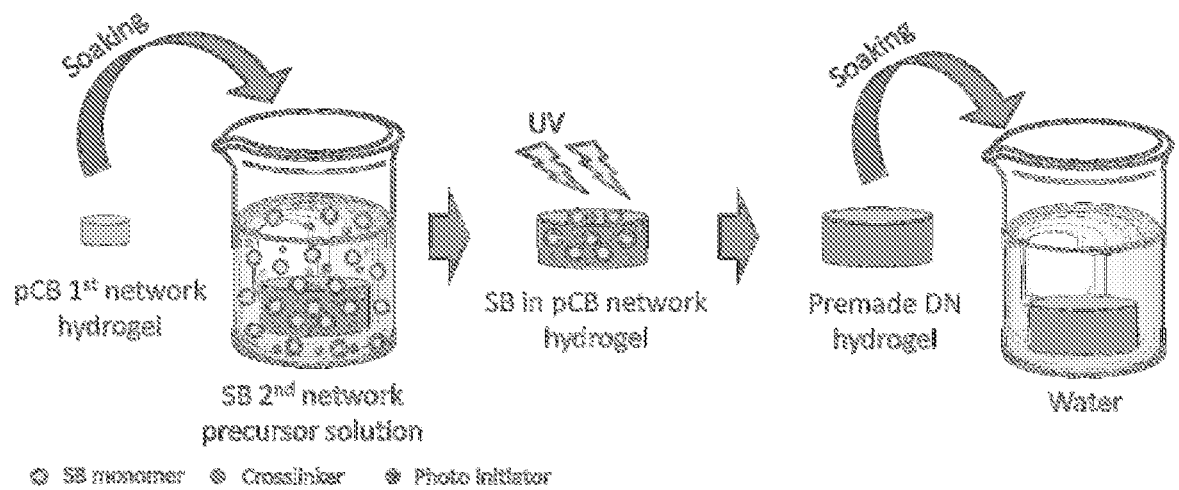
FIG. 1 is a schematic illustration of the preparation of a representative zwitterionic double network (ZDN) hydrogel of the invention, pCB/pSB ZDN hydrogel.
Figure 2A:
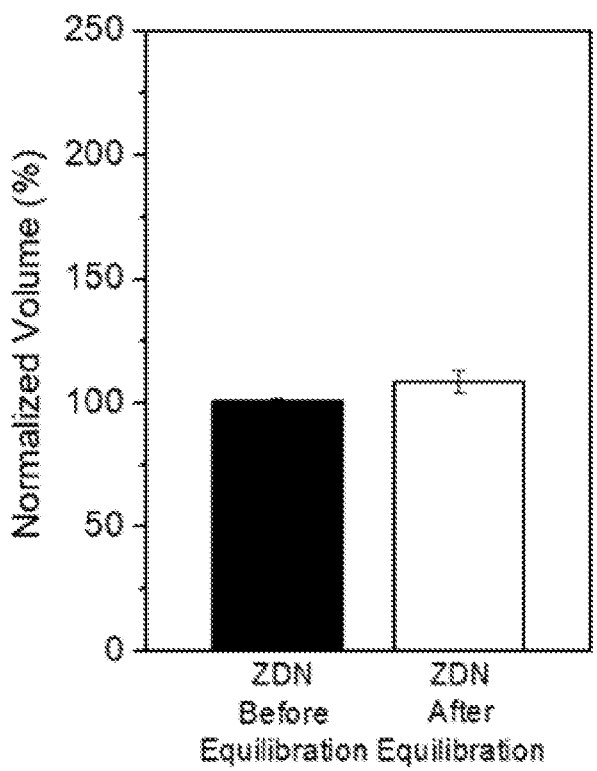
FIG. 2A compare the swelling behaviors of the as-prepared pCB/pSB ZDN hydrogel and the swollen (fully equilibrated) ZDN hydrogel after soaking in DI water. Hydrogels were made according to the composition of 1-4-0.1/4-0.1-0.01.
Figure 2B:
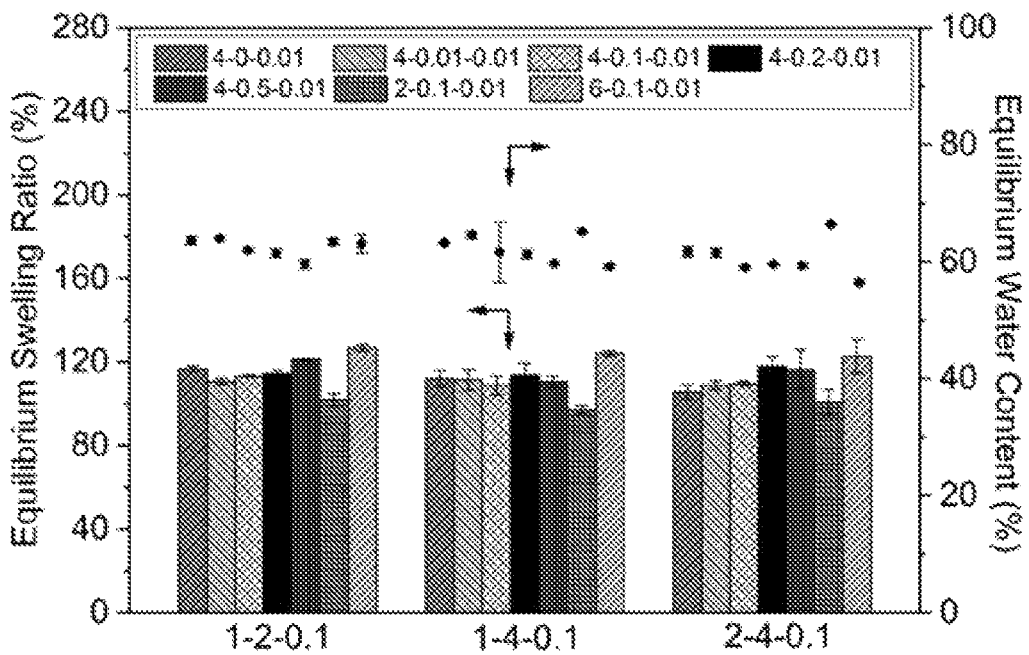
FIG. 2B compares equilibrium swelling ratios (%) and equilibrium water content (%) of pCB/pSB ZDN hydrogels with three (3) zwitterionic single network [ZSN1 (1-2-0.1, 1-4-0.1, and 2-4-0.1)] and seven (7) zwitterionic single network [ZSN2 (4-0-0.01, 4-0.01-0.01, 4-0.1-0.01, 4-0.2-0.01, 4-0.5-0.01, 2-0.1-0.01, and 6-0.1-0.01)] component ratios.
Figure 3A:
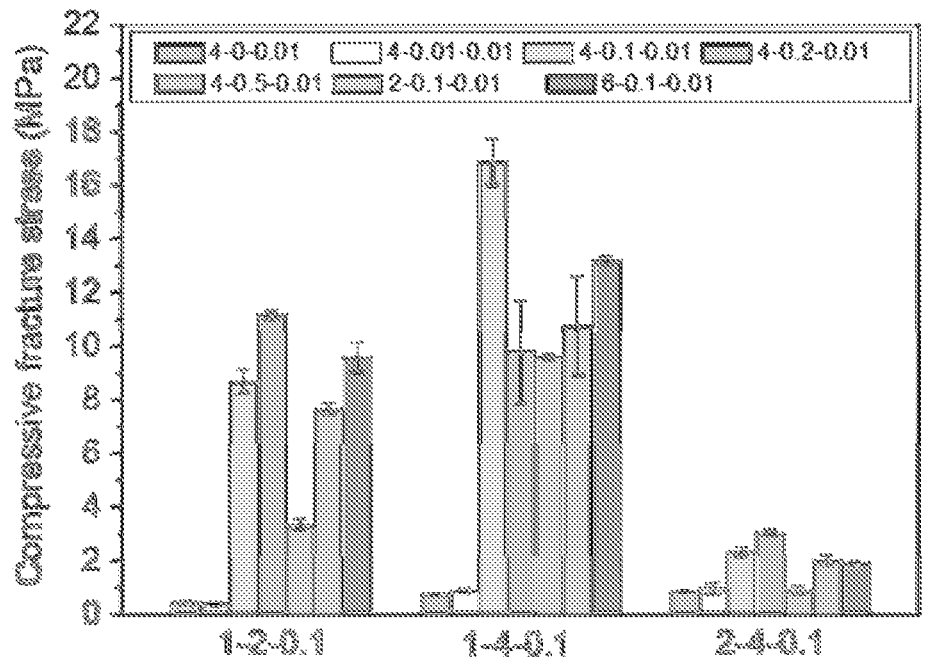
FIGS. 3A-3C compare compressive fracture stress (3A), compressive fracture strain (3B), and compressive modulus (3C) of representative pCB/pSB ZDN hydrogels with three (3) different pCB ZSN1 (1-2-0.1, 1-4-0.1, and 2-4-0.1) and seven (7) pSB ZSN2 (2-0.1-0.01, 4-0-0.01, 4-0.01-0.01, 4-0.1-0.01, 4-0.2-0.01, 4-0.5-0.01, and 6-0.1-0.01) component ratios.
Figure 3B:
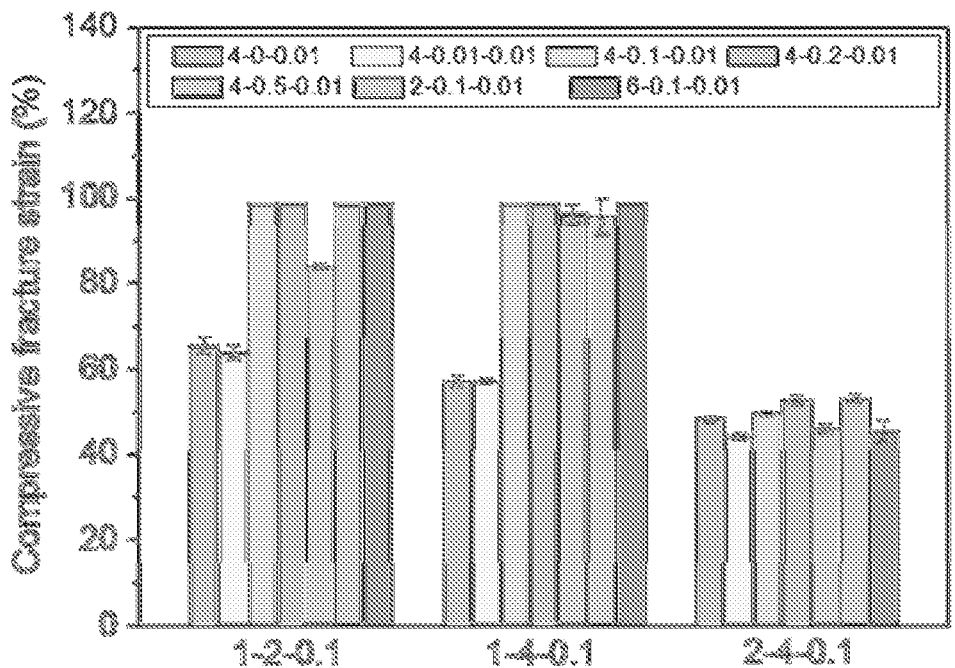
Figure 3C:
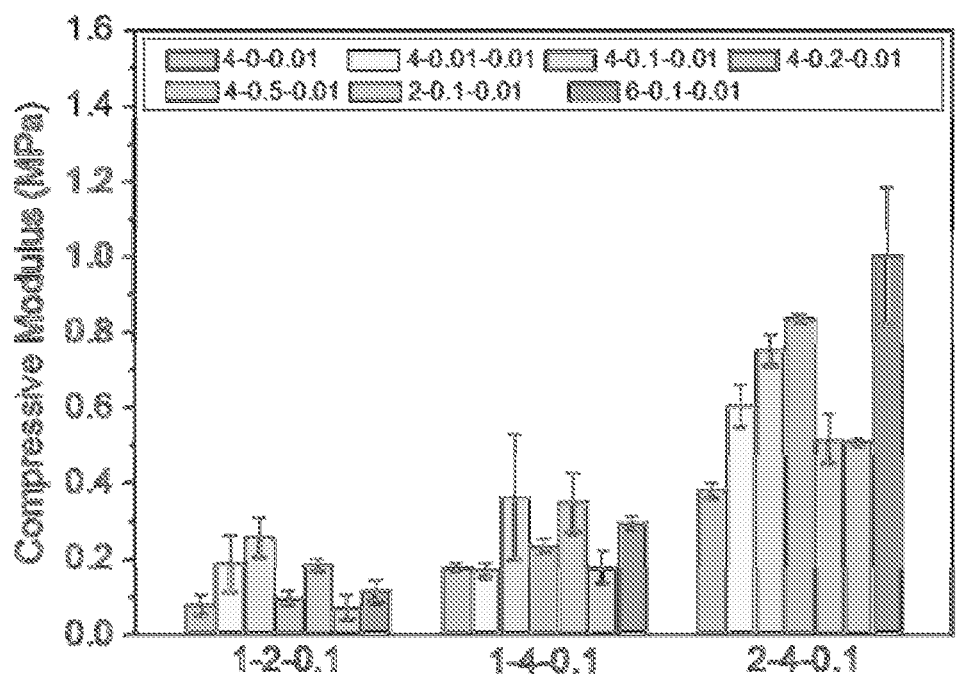

The present invention provides zwitterionic double network hydrogels, methods for making zwitterionic double network hydrogels, methods for using zwitterionic double network hydrogels, and articles made from and coated with zwitterionic double network hydrogels.

Zwitterionic Double Network Hydrogels

In one aspect, the invention provides zwitterionic double network hydrogels.

In one embodiment, the zwitterionic double network hydrogel is a double network hydrogel, comprising:
  (a) a first polymeric network comprising a first crosslinked zwitterionic polymer having from about 50 to about 100 mole percent zwitterionic moieties; and
  (b) a second polymeric network comprising a second crosslinked zwitterionic polymer having from about 50 to about 100 mole percent zwitterionic moieties,
  wherein the double network hydrogel has a compressive fracture stress of greater than about 0.9 MPa.

As used herein, the term "crosslinked" refers to both chemically crosslinked physically crosslinked polymers, unless otherwise stated.

In this embodiment, the double network hydrogel has a compressive fracture stress of greater than about 0.9 MPa. In certain of these embodiments, the compressive fracture stress of greater than about 2, 3, 5, 8, 10, 12, or 15 MPa.

It will be appreciated that although the double network hydrogel has a compressive fracture stress of greater than about 0.9 MPa, the double network hydrogel may also be characterized as having a tensile fracture stress greater than about 0.3 MPa (e.g., greater than about 0.5, 0.7, or 1.0 MPa), a tensile fracture strain greater than about 200% (e.g., greater than about 250% or 300%), or a Young's modulus greater than about 0.01 MPa (e.g., greater than about 0.1, 0.5, 1.0 MPa).

As used herein, the term "zwitterionic polymer" refers to a polymer prepared by polymerizing a polymerizable zwitterionic monomer, which provides a zwitterionic polymer having 100 mole percent zwitterionic moieties (i.e., each repeating unit of the zwitterionic polymer is a zwitterionic moiety); or refers to a polymer prepared by copolymerizing a polymerizable zwitterionic monomer and a polymerizable comonomer, which provides a zwitterionic polymer having less than 100 mole percent zwitterionic moieties (e.g., when the polymerizable zwitterionic monomer and the polymerizable comonomer are present in equal proportions in the polymerization mixture, the product is a zwitterionic polymer having 50 mole percent zwitterionic moieties).

As used herein the term "polymerizable comonomer" refers to a non-zwitterionic comonomer that is copolymerizable with a zwitterionic monomer. Representative polymerizable comonomers include acrylic acids, acrylates, methacrylic acids, methacrylates, and other comonomers include those that include hydrophilic moieties such as polyethylene oxides. The polymerizable comonomer described herein is not a polymerizable monomer that includes a zwitterionic moiety.

Representative polymerizable zwitterionic monomers and zwitterionic polymers prepared from zwitterionic monomers are described in U.S. Pat. Nos. 7,879,444 and 8,835,671, each expressly incorporated herein by reference in its entirety, as well as herein.

Representative zwitterionic polymers prepared from zwitterionic monomers have the formula:

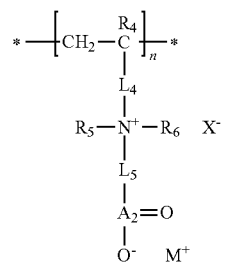

wherein $R_4$ is selected from the group consisting of hydrogen, fluorine, trifluoromethyl, C1-C6 alkyl, and C6-C12 aryl groups;

$R_5$ and $R_6$ are independently selected from the group consisting of alkyl and aryl, or taken together with the nitrogen to which they are attached form a cationic center;

$L_4$ is a linker that covalently couples the cationic center $[N^+(R_5)(R_6)]$ to the polymer backbone $[—(CH_2—CR_4)_n—]$;

$L_5$ is a linker that covalently couples the anionic center $[A_2(=O)—O^-]$ to the cationic center;

$A_2$ is C, S, SO, P, or PO;

$M^+$ is a counterion associated with the $(A_2=O)O^-$ anionic center;

$X^-$ is a counter ion associated with the cationic center;

n is an integer from 5 to about 10,000.

Representative monomers for making carboxybetaine polymers (e.g., $A_2$=C in the formula above) useful in the invention include carboxybetaine methacrylates, such as 2-carboxy-N,N-dimethyl-N-(2'-methacryloyloxyethyl) ethanaminium inner salt; carboxybetaine acrylates; carboxybetaine acrylamides; carboxybetaine vinyl compounds; carboxybetaine epoxides; and other carboxybetaine compounds with hydroxyl, isocyanates, amino, or carboxylic groups.

Representative monomers for making sulfobetaine polymers (e.g., $A_2$=SO in the formula above) useful in the invention include sulfobetaine methacrylate (SBMA), sulfobetaine acrylates, sulfobetaine acrylamides, sulfobetaine vinyl compounds, sulfobetaine epoxides, and other sulfobetaine compounds with hydroxyl, isocyanates, amino, or carboxylic groups.

The representative polymerization methods include atom transfer radical polymerization (ATRP), reversible addition fragmentation chain transfer (RAFT) polymerization, and free radical polymerization. Any conventional radical initiators for polymerization may be used to practice the current invention. The representative initiators for normal thermal or photochemical free radical polymerization include benzoyl peroxide, 2,2'-azo-bis(2-methylproionitrile) and benzoin methyl ether. Representative initiators for ATRP include alkyl halides, such as bromoisobutyryl bromide (BIBB). Representative initiators for RAFT polymerization (i.e., free radical initiators with chain reversible agency (CTA)) include thiocarbonylthio compounds.

Other zwitterionic polymers can be prepared from N-oxide monomers, as described in WO 2019/006398, expressly incorporated herein by reference in its entirety, and shown below.

In certain embodiments, the N-oxide monomer provides a polymer repeating unit that includes an N-oxide moiety that is pendant from the polymer backbone (i.e., forms a part of the polymer side chain). Representative polymers having N-oxide moieties that are pendant from the polymer backbone have the following formula:

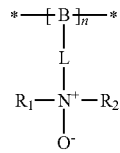

wherein

* indicates the point of attachment of the repeating unit to other repeating units in the polymer or copolymer;

B is a polymer backbone;

L is a linker group that links the N-oxide moiety to the backbone, representative groups include $—(CH_2)_x—$, $—(CH(CN))_x—$, $—C(=O)NH(CH_2)_x—$, $—C(=O)O(CH_2)_x—$, $—C(=O)OC(=O)O(CH_2)_x—$, $—(CH_2)_x—O—(CH_2)_x—$, and $—(CH_2)_x—S—S—(CH_2)_x—$, where x at each occurrence is an integer independently selected from 1 to 20;

$R_1$ and $R_2$ are independently selected from the group consisting of hydrogen, $C_1$-$C_{20}$ alkyl (including cyclic alkyl, e.g., C3-C7 cycloalkyl), and $C_6$-$C_{12}$ aryl; and n is an integer from about 10 to about 500.

In other embodiments, the N-oxide monomer provides a polymer repeating unit that includes an N-oxide moiety that is in the polymer backbone (i.e., forms a part of the polymer backbone). Representative polymers having N-oxide moieties in the polymer backbone have the following formula:

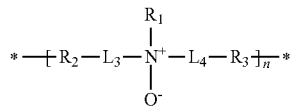

wherein
$R_1$ is selected from the group consisting of hydrogen, fluorine, trifluoromethyl, cyano, $C_1$-$C_{20}$ alkyl, and $C_6$-$C_{12}$ aryl;
$R_2$ and $R_3$ are independently selected from functional groups suitable for polymerization by addition, condensation or free radical polymerization; and
$L_3$ and $L_4$ are independently selected from $-(CH_2)_x-$, $-(CH(CN))_x-$, $-C(=O)NH(CH_2)_x-$, $-C(=O)O(CH_2)_x-$, $-C(=O)OC(=O)O(CH_2)_x-$, $-(CH_2)_xO-(CH_2)_x-$, and $-(CH_2)_x-S-S-(CH_2)_x-$, where x at each occurrence is an integer independently selected from 0 to 20, preferably from 1 to 20, and n is an integer from about 10 to about 500.

The term "zwitterionic polymer" also refers to a polymer having a substantially equal number of negative (anionic) charges and positive (cationic) charges that is prepared by copolymerizing a polymerizable negatively charged monomer and a polymerizable positively charged monomer, each present in substantially equal proportions in the polymerization mixture. The product of such a copolymerization is a zwitterionic polymer having 100 mole percent zwitterionic moieties, where each zwitterionic moiety is defined as a pair of repeating units: a repeating unit having a negative charge and a repeating unit having a positive charge. Such zwitterionic polymers are referred to as mixed charge copolymers. The term "zwitterionic polymer" also refers to a polymer prepared by copolymerizing a polymerizable negatively charged monomer, a polymerizable positively charged monomer, each present in substantially equal proportions in the polymerization mixture, and a polymerizable comonomer, which provides a zwitterionic polymer having less than 100 mole percent zwitterionic moieties (e.g., when the combination of polymerizable negatively charged monomer and polymerizable positively charged monomer and the polymerizable comonomer are present in equal proportions in the polymerization mixture (i.e., 50% combination of polymerizable negatively charged monomer and polymerizable positively charged monomer and 50% polymerizable comonomer), the product is a zwitterionic polymer having 50 mole percent zwitterionic moieties).

Representative polymerizable negatively charged monomers and polymerizable positively charged monomers and zwitterionic copolymers prepared from these monomers are described in U.S. Pat. Nos. 8,835,671 and 9,045,576, each expressly incorporated herein by reference in its entirety, as well as herein.

Representative zwitterionic polymers prepared from polymerizable negatively charged monomers and polymerizable positively charged monomers have the formula:

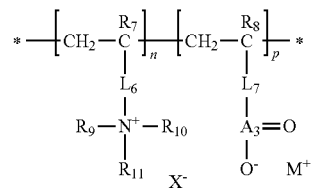

wherein
$R_7$ and $R_8$ are independently selected from hydrogen, fluorine, trifluoromethyl, C1-C6 alkyl, and C6-C12 aryl groups;
$R_9$, $R_{10}$, and $R_{11}$ are independently selected from alkyl and aryl, or taken together with the nitrogen to which they are attached form a cationic center;
$A_3(=O)-OM)$ is an anionic center, wherein $A_3$ is C, S, SO, P, or PO, and M is a metal or organic counterion;
$L_6$ is a linker that covalently couples the cationic center $[N^+(R_9)(R_{10})(R_{11})]$ to the polymer backbone;
$L_7$ is a linker that covalently couples the anionic center $[A(=O)-OM]$ to the polymer backbone;
$X^-$ is the counter ion associated with the cationic center;
n is an integer from 5 to about 10,000; and
p is an integer from 5 to about 10,000.

In one embodiment, the zwitterionic copolymer useful in the invention includes (a) a plurality of negatively charged repeating units, or a plurality of latent negatively charged repeating units; and (b) a plurality of positively charged repeating units or a plurality of positively charged repeating units, wherein the copolymer is substantially electronically neutral.

As used herein, the term "substantially electronically neutral" means that the number of positively charged repeating units and the number of the negatively charged repeating units are substantially equal, and that there is a uniform distribution of mixed charged groups at the nanometer scale.

In general, the ratio of the number of the negatively charged repeating units or the repeating units having latent negatively charged groups to the number of the positively charged repeating units or repeating units having latent positively charged groups is from about 1:1.1 to about 1:0.5. In one embodiment, the ratio of the number of the negatively charged repeating units or the repeating units having latent negatively charged groups to the number of the positively charged repeating units or repeating units having latent positively charged groups is from about 1:1.1 to about 1:0.7. In one embodiment, the ratio of the number of the negatively charged repeating units or the repeating units having latent negatively charged groups to the number of the positively charged repeating units or repeating units having latent positively charged groups is from about 1:1.1 to about 1:0.9.

In certain embodiments, the zwitterionic copolymers useful in the present invention comprise a plurality of positively charged repeating units having a positively charged pendant group. Representative positively charged pendant groups include a quaternary ammonium group, a primary amine group, a secondary amine group, a tertiary amine group, a quaternary phosphonium group, a tertiary phosphonium group, an amide group, a heteroaromatic nitrogen group, and a sulfonium group. In certain embodiments, the copolymers useful in the present invention comprise a plurality of negatively charged repeating units having a negatively charged pendant group. Representative negatively charged pendant groups include a sulfuric acid group, a carboxylic acid group, a phosphoric acid group, a nitric acid group, a phenol group, and a sulfonamide group.

In certain embodiments, the copolymers useful in the present invention comprise the repeating units having latent negatively charged groups, wherein the latent negatively charged groups are selected from the group consisting of a sulfuric acid ester group, a carboxylic acid ester group, a phosphoric acid ester group, a sulfone group, a sulfide group, a disulfide group, an ortho ester group, an anhydride group, and a beta-ketosulfone group. In certain embodiments, the copolymers useful in the present invention comprise the repeating units having latent positively charged groups, wherein the latent positively charged groups are selected from the group consisting of an imide group and an oxyimino group.

The latent negatively charged groups and latent positively charged groups in the copolymers useful in the present invention can be converted to charged groups upon exposure to an oxidant, a reductant, heat, light, an acid, a base, an enzyme, or electromagnetic field.

The negatively charged repeating unit maybe a repeating unit having a negatively charged pendant group or a repeating unit having a negative charge in its monomeric backbone structure. The negatively charged pendant group can be any group with a negative charge. Representative negatively charged pendant groups include sulfuric acid groups, sulfonic acid groups, carboxylic acid groups, phosphoric acid groups, phosphonic acid groups, phenol groups, and sulfonamide groups.

The negatively charged repeating unit can be derived from a monomer having a negatively charged pendant group or a negatively charged backbone. Representative monomers that can be used to derive the negatively charged repeating unit copolymers in the copolymers useful in the present invention include 2-carboxyethyl acrylate, 3-sulfopropyl methacrylate, lauryl methacrylate, isobutyl methacrylate, 2,2,2-trifluroethyl methacrylate, and poly(ethylene glycol) methacrylate, and D-glucuronic acid.

The positively charged repeating unit may be a repeating unit having a positively charged pendant group or a repeating unit having a positive charge on its monomeric backbone structure. The positively charged pendant group can be any group with a positive charge. Representative positively charged pendant groups include quaternary ammonium groups, primary amine groups, secondary amine groups, tertiary amine groups, quaternary phosphonium groups, tertiary phosphonium groups, amide groups, heteroaromatic nitrogen groups, sulfonium groups, and metallic organic acids.

The positively charged repeating unit can be derived from a monomer having a positively charged pendant group or a positively charged backbone. Representative monomers that can be used to derive the positively charged repeating unit in the copolymers useful in the present invention include 2-(dimethylamino)ethyl methacrylate, 2-(diethylamino) ethyl methacrylate, [2-(methacryloyloxy)ethyl] trimethylammonium chloride, and N-acetylglucosamine.

It will be appreciated that the polymerizable zwitterionic monomer, the polymerizable negatively charged monomers, and the polymerizable positively charged monomers, can be non-charged (e.g., protected) monomers in which the non-charged monomers can be polymerized as described herein and then further reacted (e.g., by chemical stimuli or environmental stimuli, such as pH) to reveal the counterpart zwitterionic, negatively charged, or positively charged moieties in the product zwitterionic polymers. Such non-charged monomers are considered to be latent monomers that reveal their zwitterionic, negatively charged, or positively charged counterparts.

Representative non-charged (latent) monomers are described in U.S. Pat. Nos. 8,268,301 and 8,349,966, each expressly incorporated herein by reference in its entirety, as well as herein.

In another embodiment, the zwitterionic double network hydrogel is a double network hydrogel, comprising:
(a) a first chemical polymeric network comprising a first crosslinked zwitterionic polymer having from about 50 to about 100 mole percent zwitterionic moieties; and
(b) a second chemical polymeric network comprising a second zwitterionic polymer having from about 50 to about 100 mole percent zwitterionic moieties.

In this embodiment, it will be appreciated that the first crosslinked zwitterionic polymer is a chemically crosslinked zwitterionic polymer, and that the second crosslinked zwitterionic polymer is a chemically crosslinked zwitterionic polymer.

As used herein, the term "chemical polymeric network" refers to a polymeric network that is prepared by a chemical method; specifically by polymerization. In the double network of the invention, each of the first and second network is prepared by polymerization. More specifically, once the first chemical polymeric network is prepared, a second chemical polymeric network is prepared by polymerizing a suitable polymerizable monomer (or copolymerizing suitable comonomers) in the presence of the first polymeric network (e.g., polymerizing the suitable polymerizable monomer in a solution that includes first polymeric network). Chemical polymeric networks are distinguished from physical networks, which are prepared from polymers (or copolymers) by mechanical means and include interpolymer crosslinking, such as ionic, hydrogen bonding, and dipole-dipole crosslinking. Accordingly, double networks can be chemical-chemical networks, chemical-physical networks, or physical-physical networks. Physical, chemical, and chemical-physical double networks of zwitterionic hydrogels are described in Jiang et al., *J. Phys. Chem. B* 2008, 112: 5327-5332.

In a further embodiment, the zwitterionic double network hydrogel is a double network hydrogel, comprising:
(a) a first polymeric network comprising a first crosslinked zwitterionic polymer having from about 50 to about 100 mole percent zwitterionic moieties, wherein the first crosslinked zwitterionic polymer is not a poly(sulfobetaine); and
(b) a second polymeric network comprising a second crosslinked zwitterionic polymer having from about 50 to about 100 mole percent zwitterionic moieties.

In another embodiment, the zwitterionic double network hydrogel is a double network hydrogel, comprising:
(a) a first polymeric network comprising a first crosslinked polymer, wherein the first polymeric network is a hydrogel; and
(b) a second polymeric network comprising a second crosslinked zwitterionic polymer having from about 50 to about 100 mole percent zwitterionic moieties,
wherein the double network hydrogel has a compressive fracture stress of greater than about 0.9 MPa.

In certain of these embodiments, the first crosslinked polymer is a zwitterionic polymer, a polysaccharide, or a collagen. Representative first crosslinked polymers include hyaluronic acids, alginates, or dextrans.

In this embodiment, the double network hydrogel has a compressive fracture stress of greater than about 0.9 MPa. In certain of these embodiments, the compressive fracture stress of greater than about 2, 3, 5, 8, 10, 12, or 15 MPa.

It will be appreciated that although the double network hydrogel has a compressive fracture stress of greater than about 0.9 MPa, the double network hydrogel may also be characterized as having a tensile fracture stress greater than about 0.3 MPa (e.g., greater than about 0.5, 0.7, or 1.0 MPa), a tensile fracture strain greater than about 200% (e.g., greater than about 250% or 300%), or a Young's modulus greater than about 0.01 MPa (e.g., greater than about 0.1, 0.5, 1.0 MPa).

In a further embodiment, the zwitterionic double network hydrogel is a double network hydrogel, comprising:
(a) a first polymeric network comprising a first crosslinked polymer, wherein the first polymeric network is a hydrogel; and
(b) a second polymeric network comprising a crosslinked poly(sulfobetaine) having from about 50 to about 100 mole percent zwitterionic moieties.

In certain of these embodiments, the first crosslinked polymer is a zwitterionic polymer, a polysaccharide, or a collagen. Representative first crosslinked polymers include hyaluronic acids, alginates, or dextrans.

In certain of the double network hydrogels described above, the first crosslinked zwitterionic polymer is a poly(carboxybetaine) (pCB), poly(sulfobetaine) (pSB), poly(sulfabetaine) (pSAB), poly(phosphobetaine) (pPB), poly(phosphorylcholine) (pPC), poly(choline phosphate) (pCP), poly(trimethylamine-N-oxide) (pTMAO), or a latent derivative thereof.

In certain of the double network hydrogels described above, the second crosslinked zwitterionic polymer is a poly(carboxybetaine) (pCB), poly(sulfobetaine) (pSB), poly(sulfabetaine) (pSAB), poly(phosphobetaine) (pPB), poly(phosphorylcholine) (pPC), poly(choline phosphate) (pCP), poly(trimethylamine-N-oxide) (pTMAO), or a latent derivative thereof.

In certain of the double network hydrogels described above, the first crosslinked zwitterionic polymer is a poly(carboxybetaine) (pCB) and the second crosslinked zwitterionic polymer is a poly(sulfobetaine) (pSB).

In certain of the double network hydrogels described above, the first crosslinked zwitterionic polymer is a poly(sulfobetaine) (pSB) and the second crosslinked zwitterionic polymer is a poly(sulfobetaine) (pSB).

In certain of the double network hydrogels described above, the first crosslinked zwitterionic polymer is a poly(trimethylamine-N-oxide) (pTMAO) and the second crosslinked zwitterionic polymer is a poly(sulfobetaine) (pSB).

In certain of the double network hydrogels described above, the first crosslinked zwitterionic polymer is a poly(phosphorylcholine) (pPC) and the second crosslinked zwitterionic polymer is a poly(sulfobetaine) (pSB).

In certain of the double network hydrogels described above, the first crosslinked polymer is a zwitterionic polymer crosslinked with a metal ion selected from $Fe^{3+}$, $Ca^{2+}$, $Mg^{2+}$, $Cu^{2+}$, and $Zn^{2+}$.

In certain of the double network hydrogels described above, the second crosslinked zwitterionic polymer is a poly(sulfobetaine).

In certain of the above embodiments, the zwitterionic moieties are selected from $-N(CH_3)_3^+$ and $-SO_3^-$, or $-N(CH_3)_3^+$ and $-SO_4^-$.

The zwitterionic double network hydrogels described herein have advantageous mechanical strength characterized as having one or more of a compressive fracture stress greater than about 0.9 MPa (e.g., greater than about 2, 3, 5, 8, 10, 12, or 15 MPa); a tensile fracture stress greater than about 0.3 MPa (e.g., greater than about 0.5, 0.7, or 1.0 MPa); a tensile fracture strain greater than about 200% (e.g., greater than about 250% or 300%); or a Young's modulus greater than about 0.01 MPa (e.g., greater than about 0.1, 0.5, or 1.0 MPa).

For the zwitterionic double network hydrogels described herein, in certain embodiments, the first polymeric network is chemically crosslinked or physically crosslinked, and the second polymeric network is chemically crosslinked or physically crosslinked. As used herein, the term "physically crosslinked" refers to crosslinking between polymers through ionic interactions, hydrogen bonding interactions, and/or dipole-dipole interactions.

The zwitterionic double network hydrogels described herein have advantageous nonfouling properties characterized as having a fibrinogen binding level of less than about 20% (e.g., less than about 15% or less than about 10%) relative to that of tissue culture polystyrene (TCPS) tested via a fibrinogen binding assay (wherein the polymer surface is incubated at 37° C. for 90 minutes with a 1.0 mg/mL fibrinogen solution in 0.15 M phosphate buffered saline at pH 7.4).

The zwitterionic double network hydrogels described herein have water contents greater than about 50% (e.g., greater than about 70%, 80%, or 90%) and low or no swelling (i.e., a swelling ratio, $V_{2e}/V_2$, less than 2, where $V_2$ is the volume of ZDN hydrogel in the as-prepared state and $V_{2e}$ is the volume of ZDN hydrogel soaked in DI water or 0.15 M phosphate buffered saline at pH 7.4 until equilibrium is reached).

As described herein, in certain embodiments, the zwitterionic double network hydrogels have at least 50 mole percent zwitterionic moieties (e.g., 60, 70, 80, 90, 100 mole percent). Higher zwitterionic content is preferred for imparting nonfouling properties to the hydrogel as long as the advantageous mechanical properties are achieved.

Figure 4:
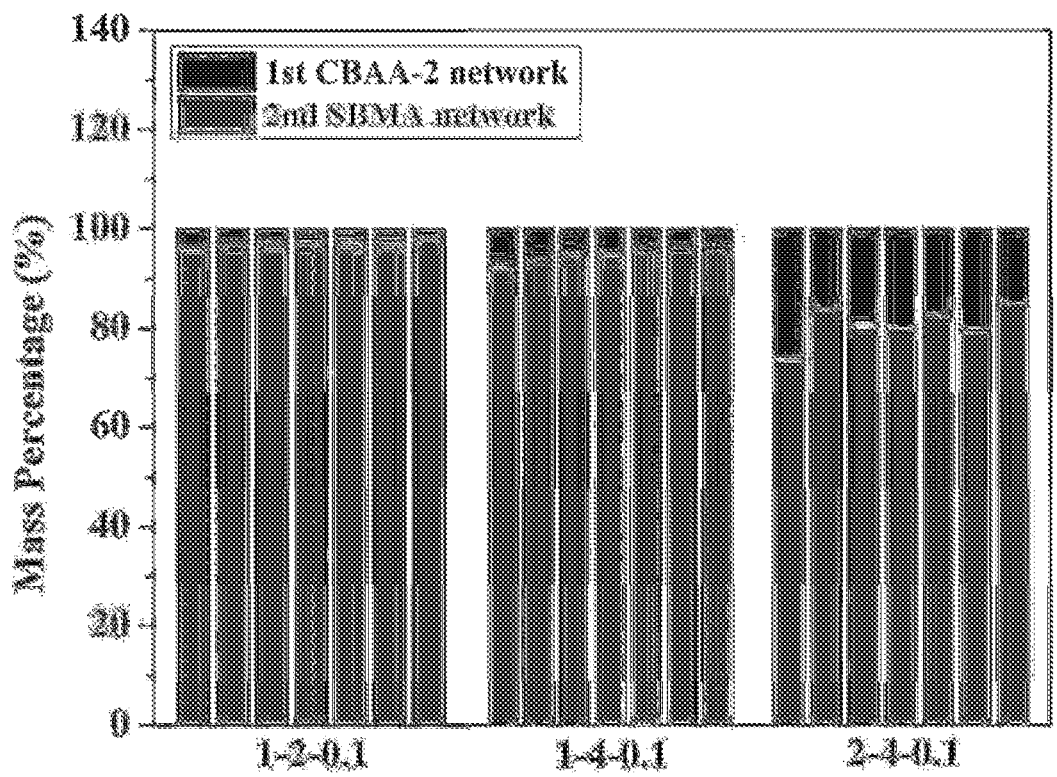
FIG. 4 compares the mass percentage of representative pCB/pSB ZDN hydrogels with three (3) different pCB ZSN1 (1-2-0.1, 1-4-0.1, and 2-4-0.1) and seven (7) pSB ZSN2 (2-0.1-0.01, 4-0-0.01, 4-0.01-0.01, 4-0.1-0.01, 4-0.2-0.01, 4-0.5-0.01, and 6-0.1-0.01) component ratios.
Figure 5A:
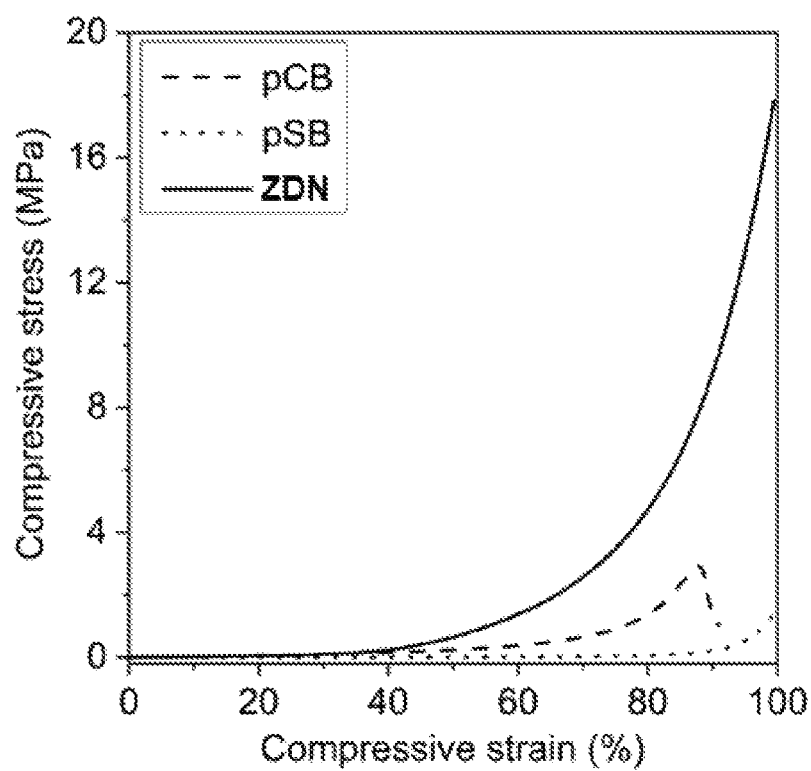
FIGS. 5A and 5B compare representative uniaxial compressive curves (5A) and compressive modulus, fracture stress, and fracture strain (5B) of representative pCB/pSB ZDN hydrogels (1-4-0.1/4-0.1-0.01), a pCB single network (SN) hydrogel (1-4-0.1), and a pSB single network (SN) hydrogel (4-0.1-0.01).
Figure 5B:
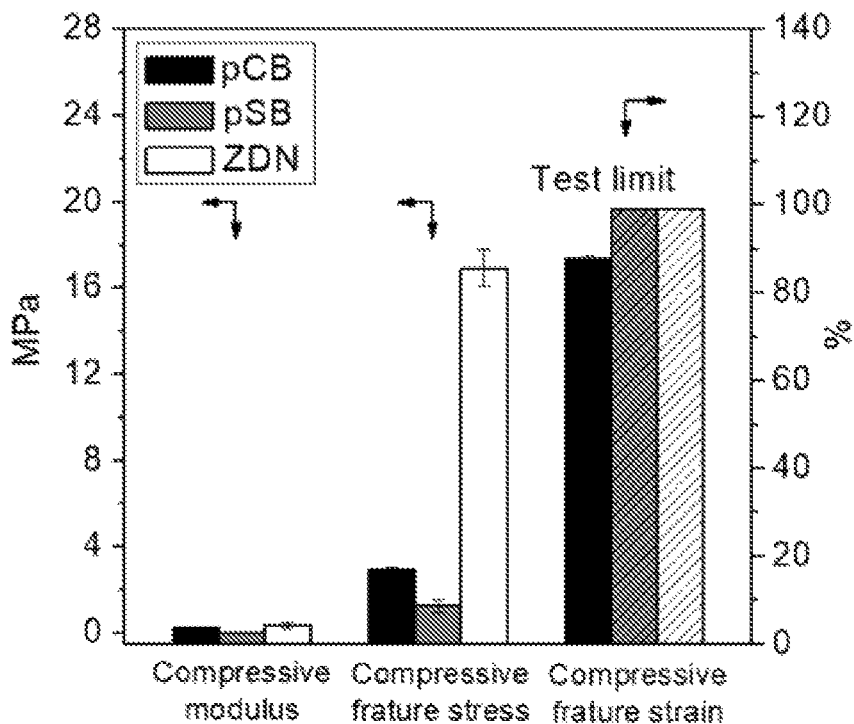
Figure 6A:
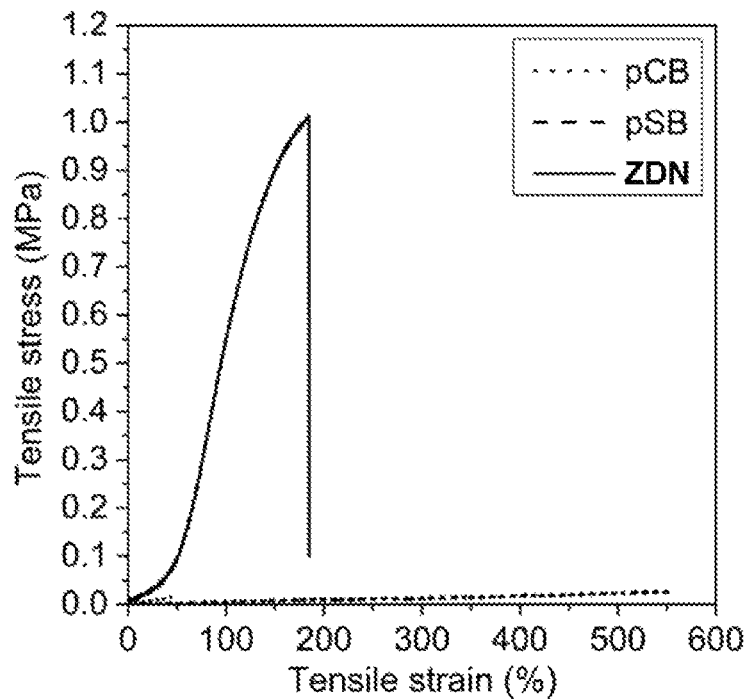
FIGS. 6A and 6B compare representative tensile curves (6A) and tensile modulus, fracture stress, and fracture strain (6B) of representative pCB/pSB ZDN hydrogels (1-4-0.1/4-0.1-0.01), a pCB single network hydrogel (SN, 1-4-0.1) and a pSB single network hydrogel (SN, 4-0.1-0.01).
Figure 6B:
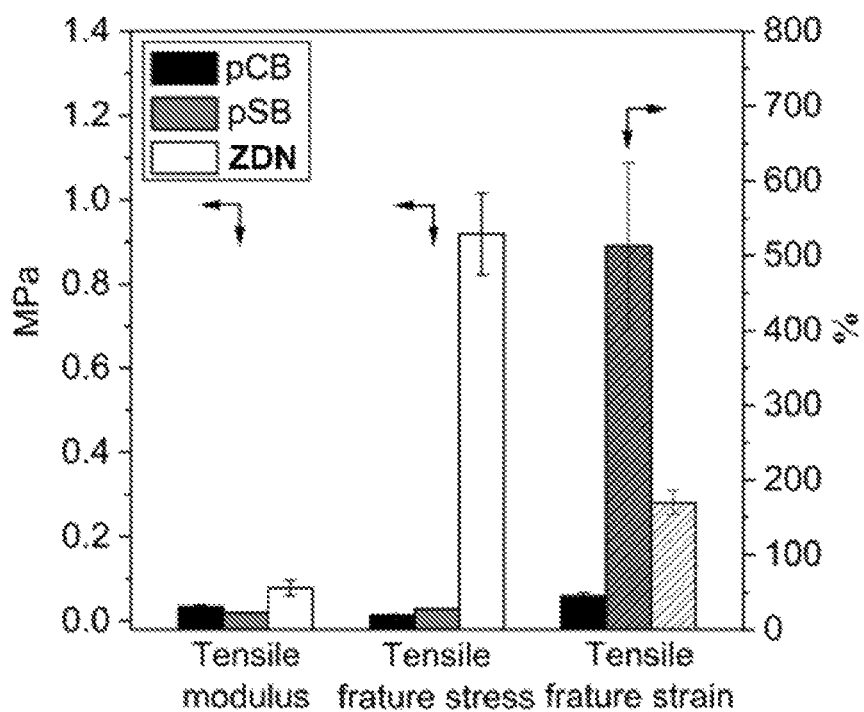
Figure 7A:
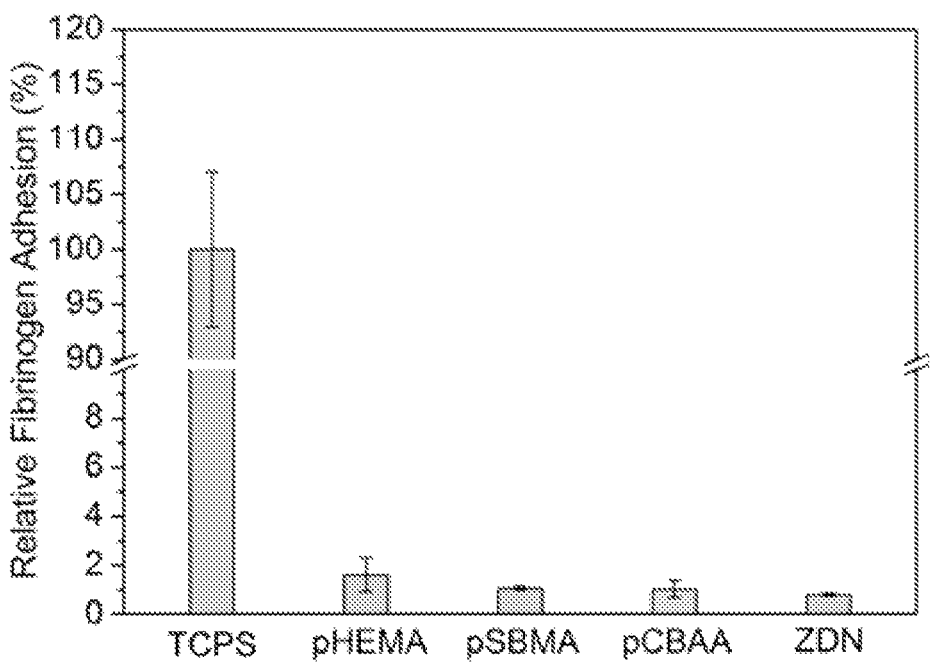
FIGS. 7A-7F compare relative nonfouling (protein and cell adhesion) of representative zwitterionic double network (pCB/pSB ZDN) hydrogel (1-4-0.1/4-0.1-0.01) surfaces: human fibrinogen (7A), proteins in undiluted human serum (7B), rat platelets (7C), RIN-m5F cells (7D), and DC 2.4 cells (7E). All the data were normalized with respect to tissue culture polystyrene (TCPS). Optical images of RIN-m5F cells and DC 2.4 cells respectively adhered on TCPS and pCB/pSB ZDN hydrogel surfaces are compared in FIG. 7F. The magnification of all images was 200×.
Figure 7B:
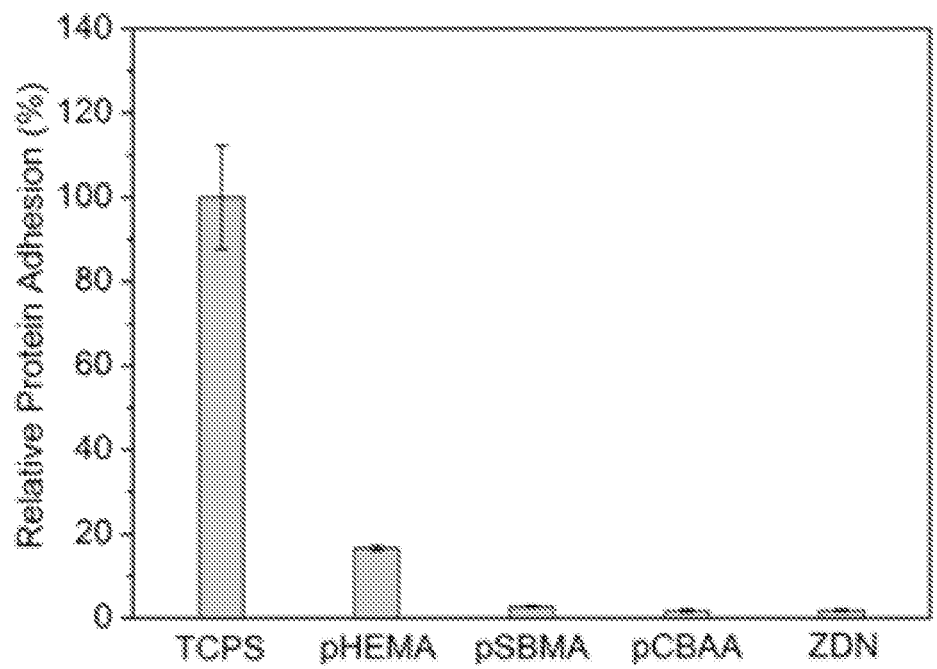
Figure 7C:
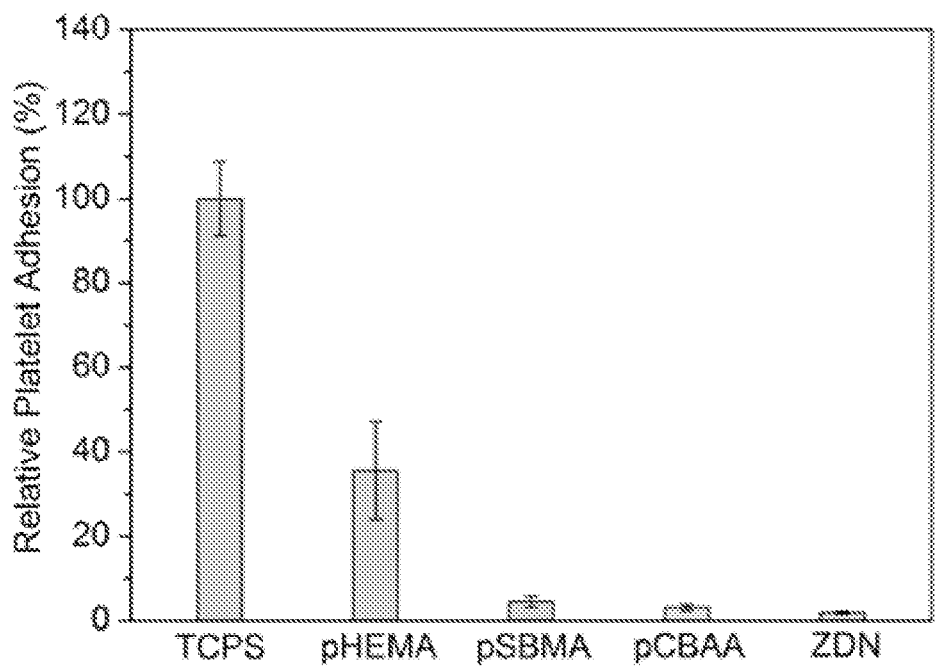
Figure 7D:
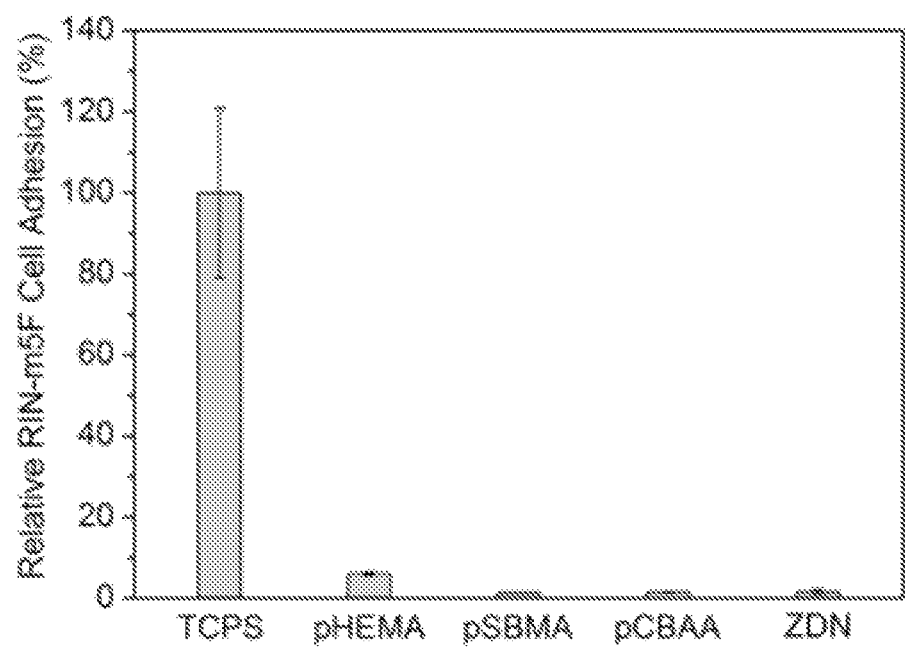
Figure 7E:
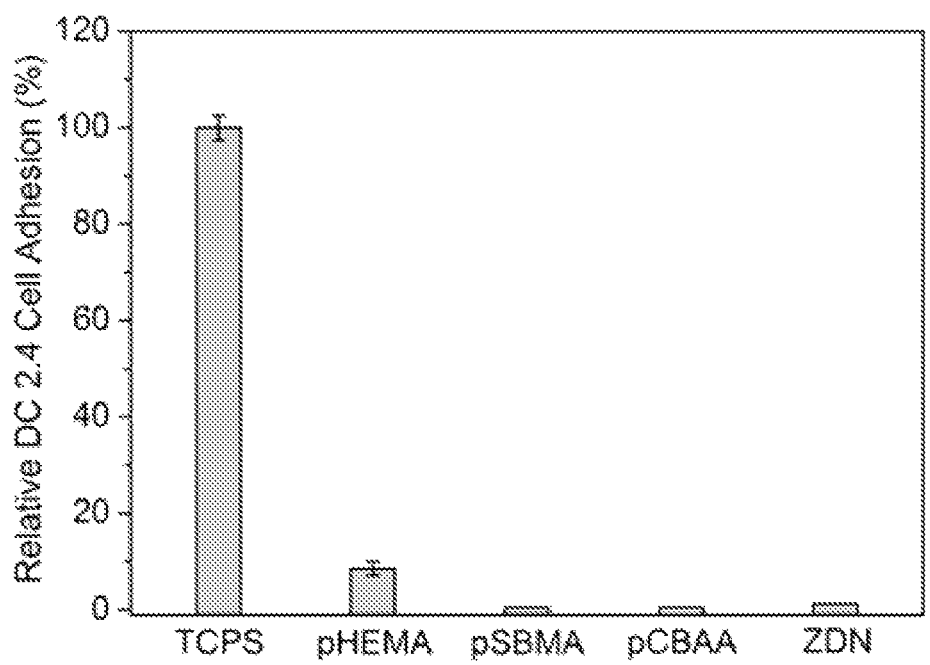
Figure 7F:
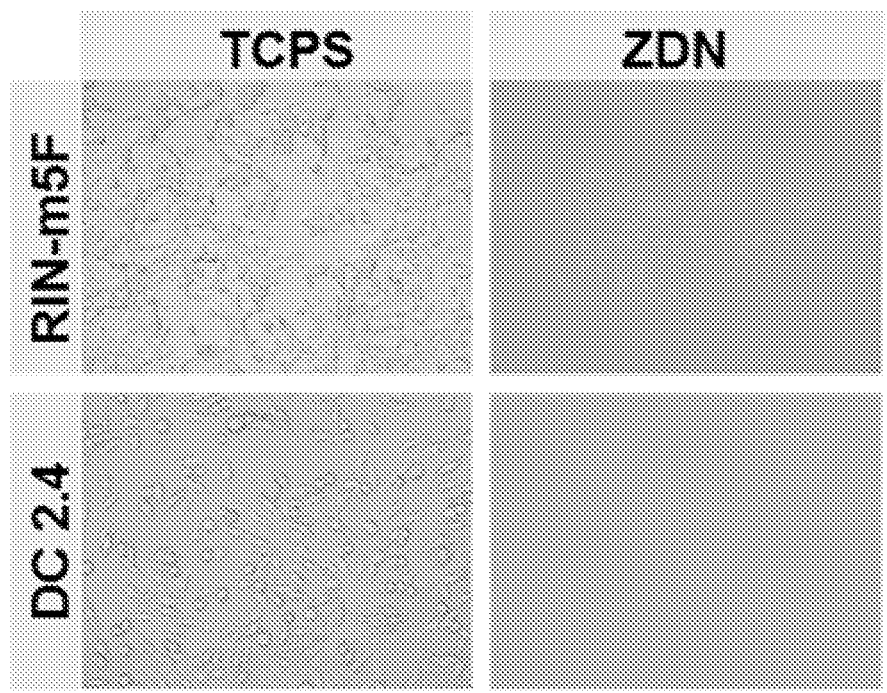
Figure 8A:
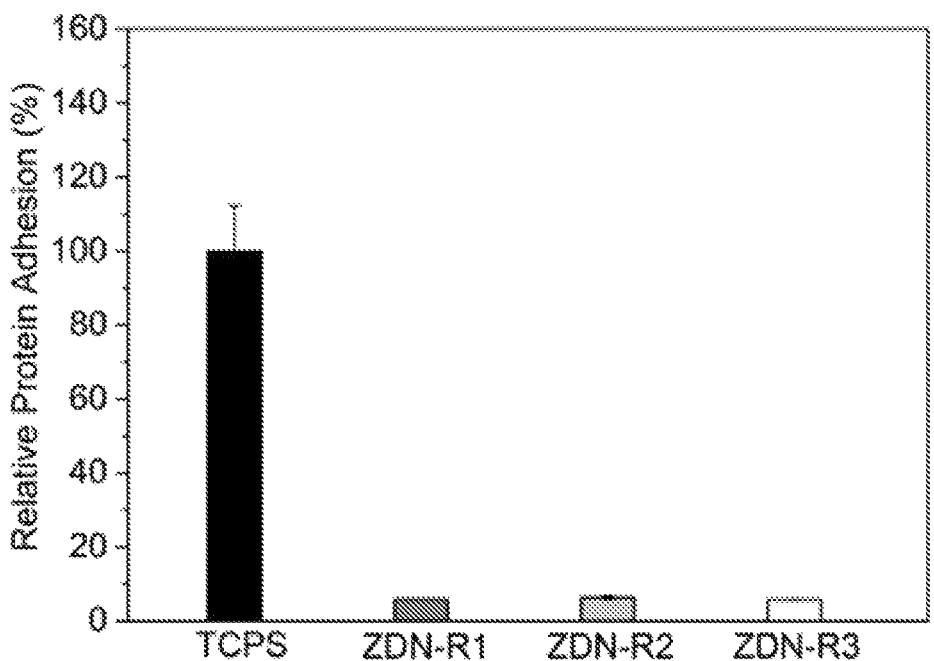
FIGS. 8A-8D compare relative nonfouling (protein and cell adhesion) of representative zwitterionic double network (pCB/pSB ZDN) hydrogel (1-4-0.1/4-0.1-0.01) surfaces after three rounds of autoclaving (ZDN-R1, ZDN-R2 and ZDN-R3): proteins in undiluted human serum (8A), rat platelets (8B), RIN-m5F cells (8C), and DC 2.4 cells (8D). All the data were normalized with respect to TCPS.
Figure 8B:
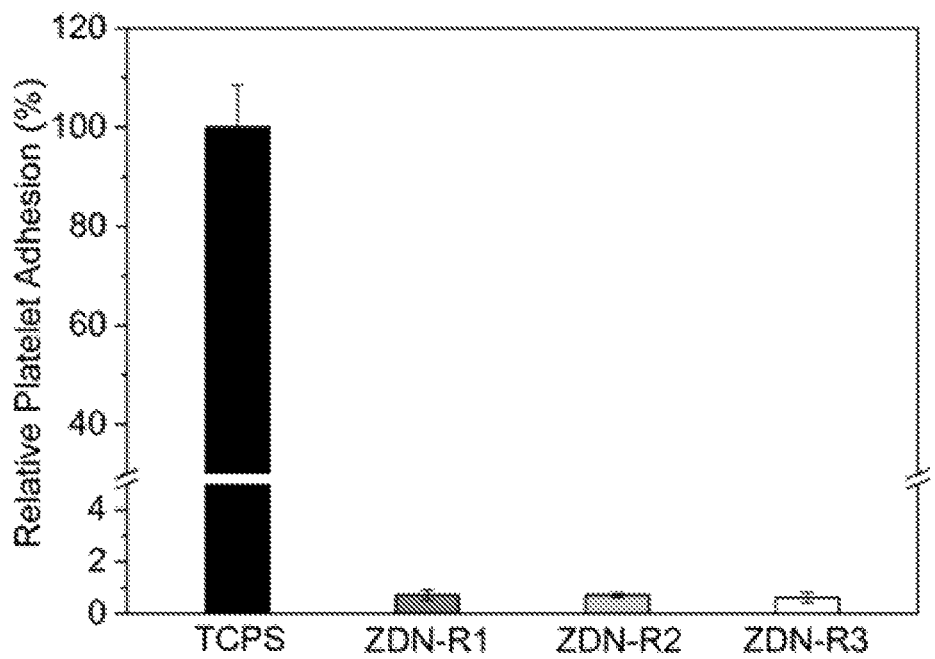
Figure 8C:
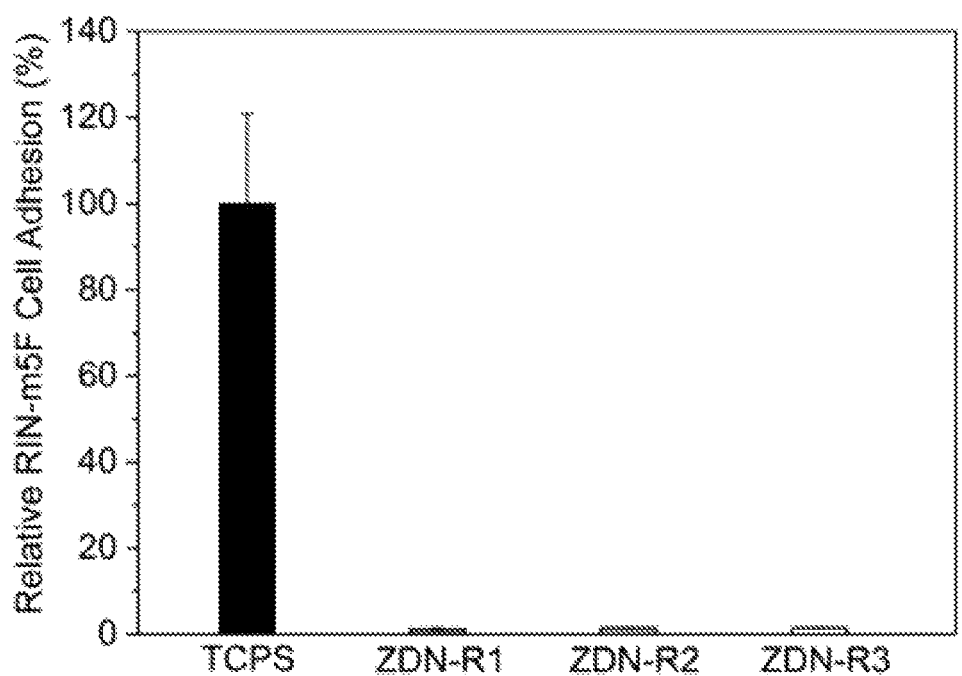
Figure 8D:
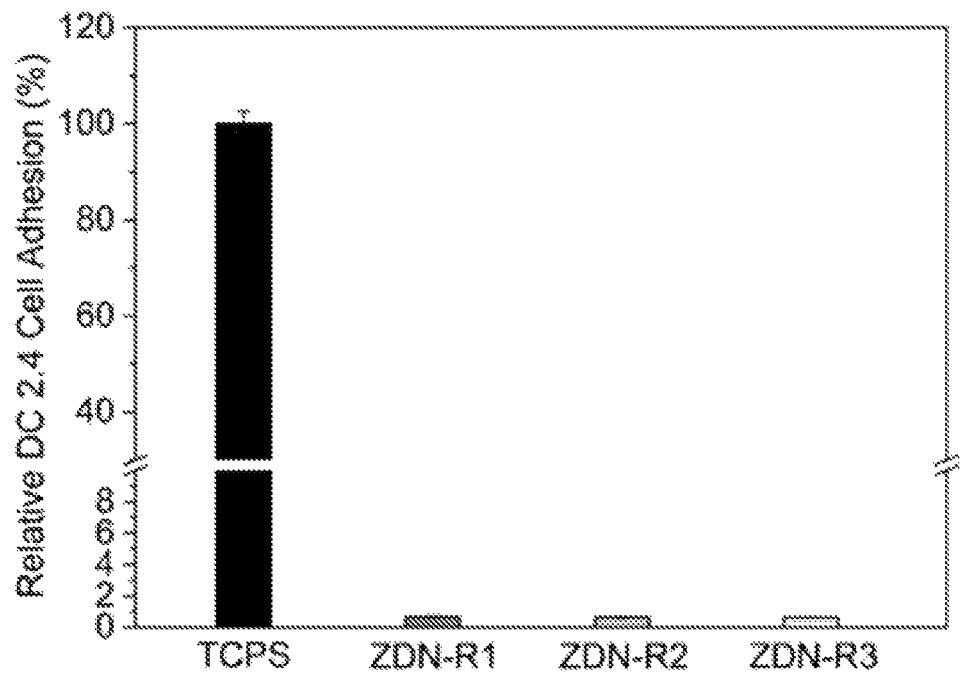
Figure 9A:
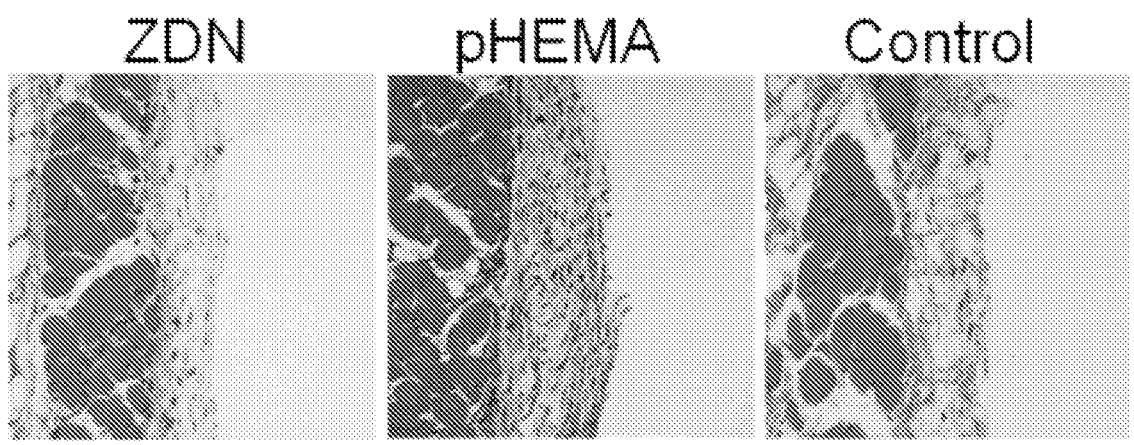
FIGS. 9A-9C compare hemotoxylin and eosin (H&E) staining for skin tissues with a representative pCB/pSB ZDN hydrogel (1-4-0.1/4-0.1-0.01) after one week of implantation compared to pHEMA and Control (9A); Masson's trichrome staining for skin tissues with a representative pCB/pSB ZDN hydrogel (1-4-0.1/4-0.1-0.01) after implantation for 1, 4, and 12 weeks compared to pHEMA; images of implanted mice and retrieved representative pCB/pSB ZDN hydrogels (1-4-0.1/4-0.1-0.01) and Masson's trichrome staining for skin tissues with pCB/pSB ZDN hydrogels after implantation for 24 weeks. Skin tissues of mice without implants were set as control. The magnification of all tissue staining images was 100×.
Figure 9B:
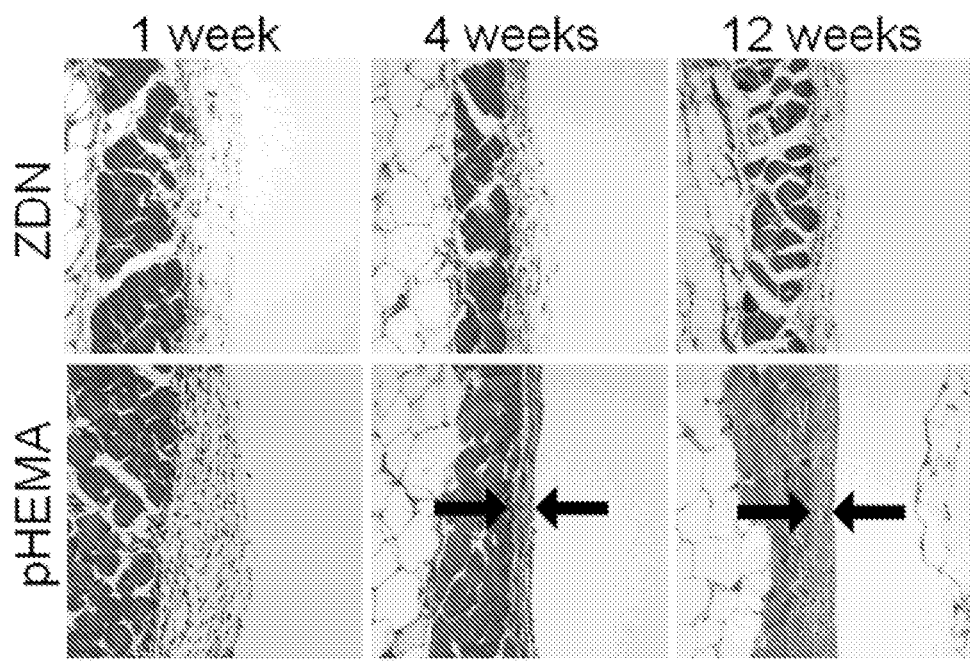
Figure 9C:
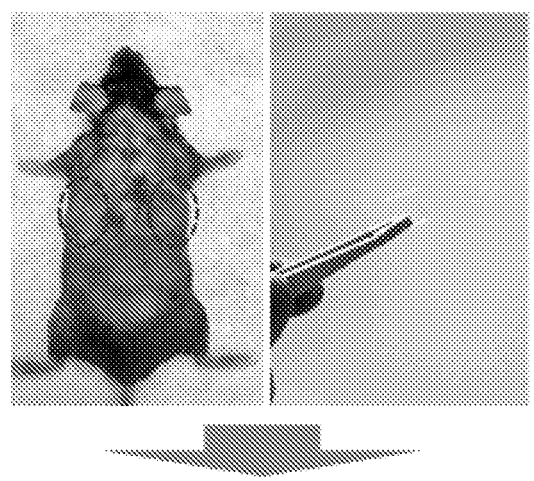
Figure 9C:
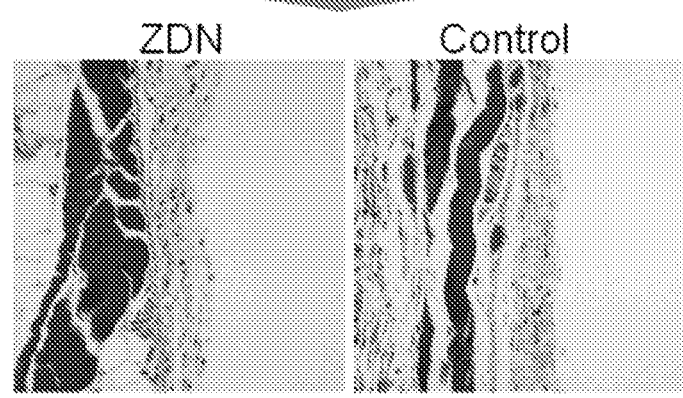
Figure 10:
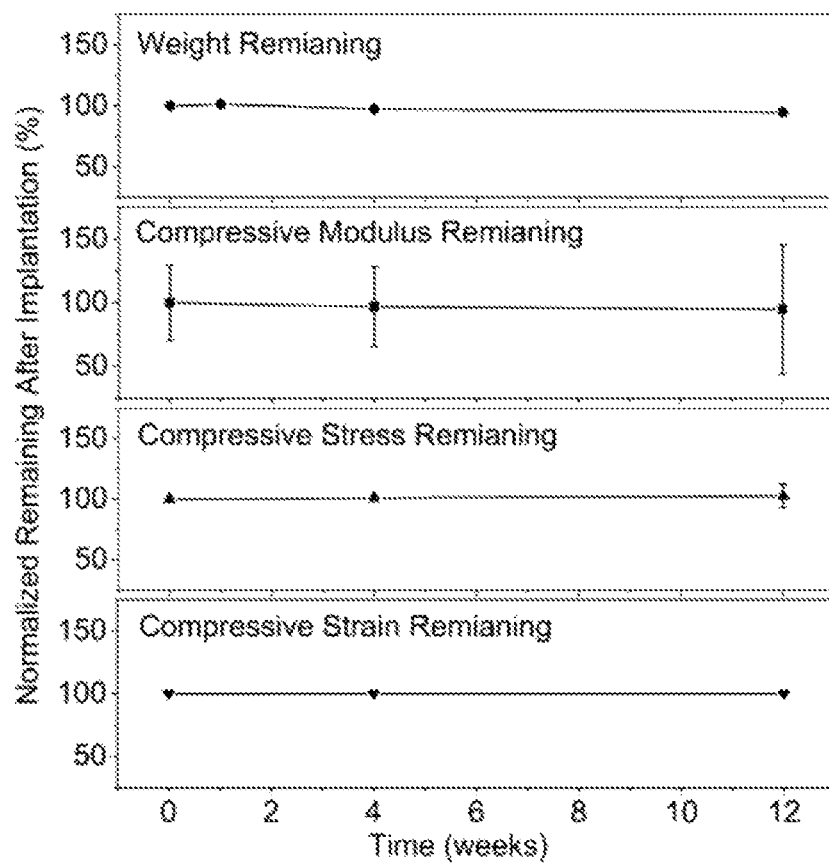
FIG. 10 compares degradation (weight remaining) and mechanical properties (compressive modulus remaining, compressive stress remaining, compressive strain remaining) of representative pCB/pSB ZDN hydrogels (1-4-0.1/4-0.1-0.01) after implantation for 12 weeks.
Figure 11A:
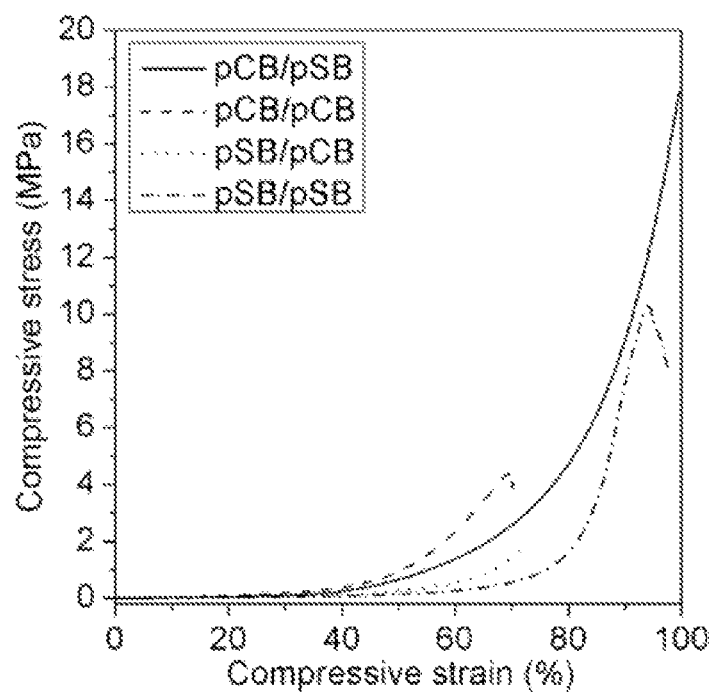
FIGS. 11A-11C compare compressive stress curves (11A), compressive modulus, fracture stress, and fracture strain (11B), and equilibrium swelling ratios and equilibrium water contents for representative ZDN hydrogels of the invention: pCB/pSB, pCB/pCB, pSB/pCB, pSB/pSB ZDN hydrogels. pCB/pSB and pSB/pSB ZDN hydrogels were made according to the composition of 1-4-0.1/4-0.1-0.01 and pCB/pCB and pSB/pCB ZDN hydrogels were made according to the composition of 1-4-0.1/4-0.2-0.01.
Figure 11B:
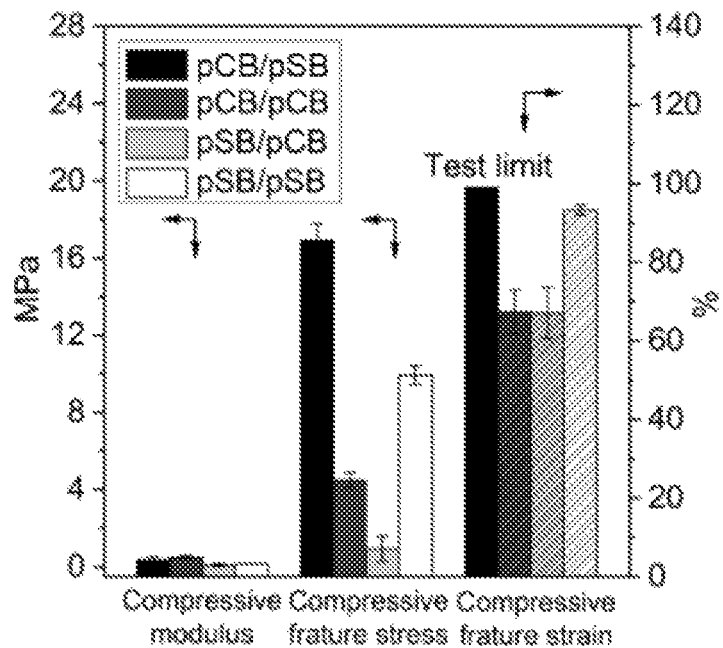
Figure 11C:
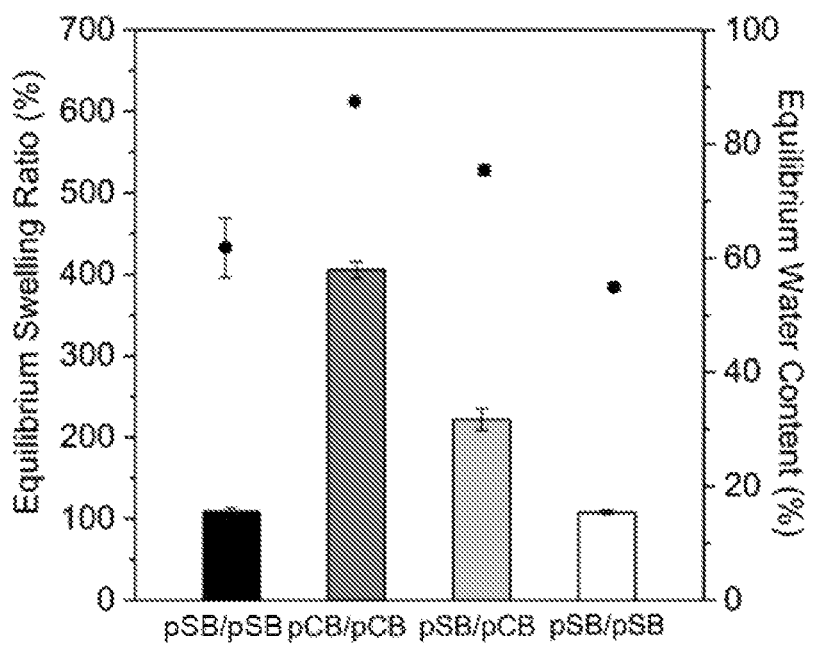
Figure 12A:
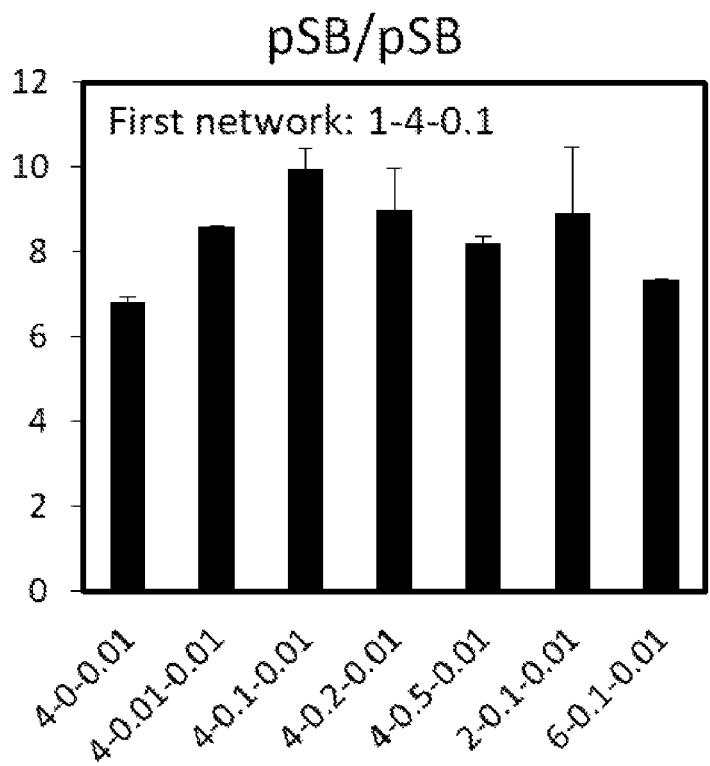
FIGS. 12A-12C compare compression tests of representative ZDN hydrogels: pSB/pSB (12A), pCB/CB (12B), and pSB/CB (12C). In each, the first networks of ZDN hydrogels were made according to the composition of 1-4-0.1. The second networks of the ZDN hydrogels were made according to the seven (7) different compositions as indicated in the figure.
Figure 12B:
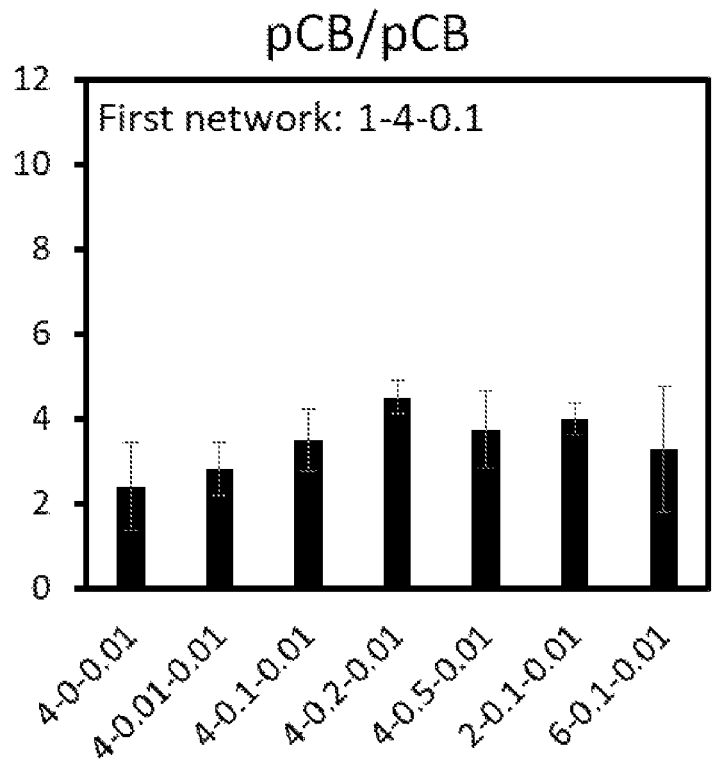
Figure 12C:
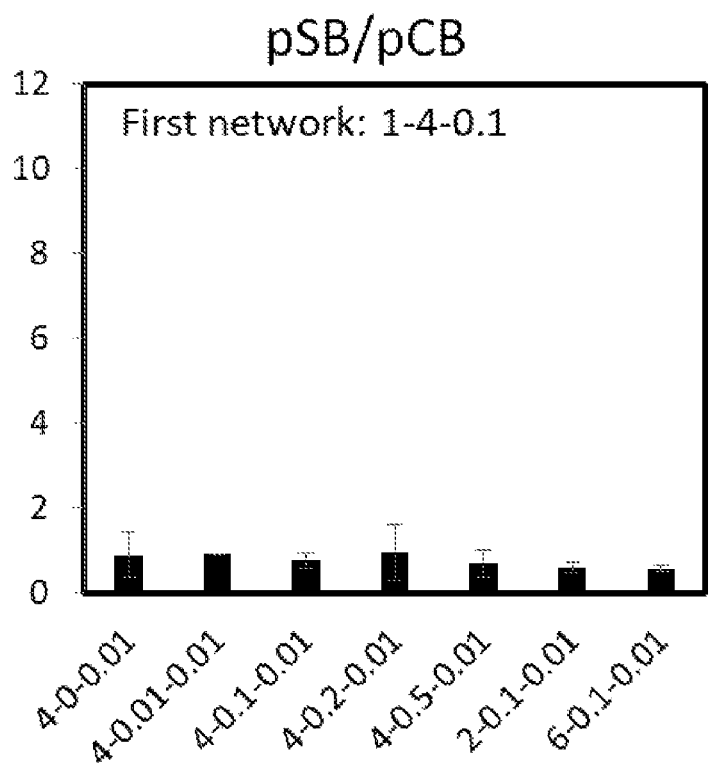
Figure 13A:
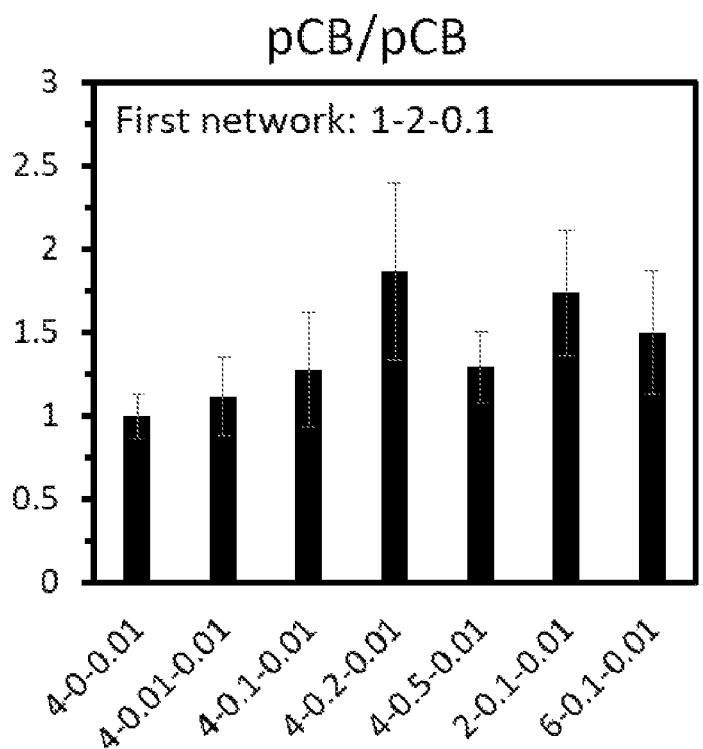
FIGS. 13A-13C compare compression tests of representative pCB/CB ZDN hydrogels: the first network of hydrogels were made according to the composition of 1-2-0.1 (13A), 1-4-0.1 (13B), and 2-4-0.1 (13C). The second network of the pCB/pCB ZDN hydrogels were made according to the seven (7) different compositions as indicated in the figure.
Figure 13B:
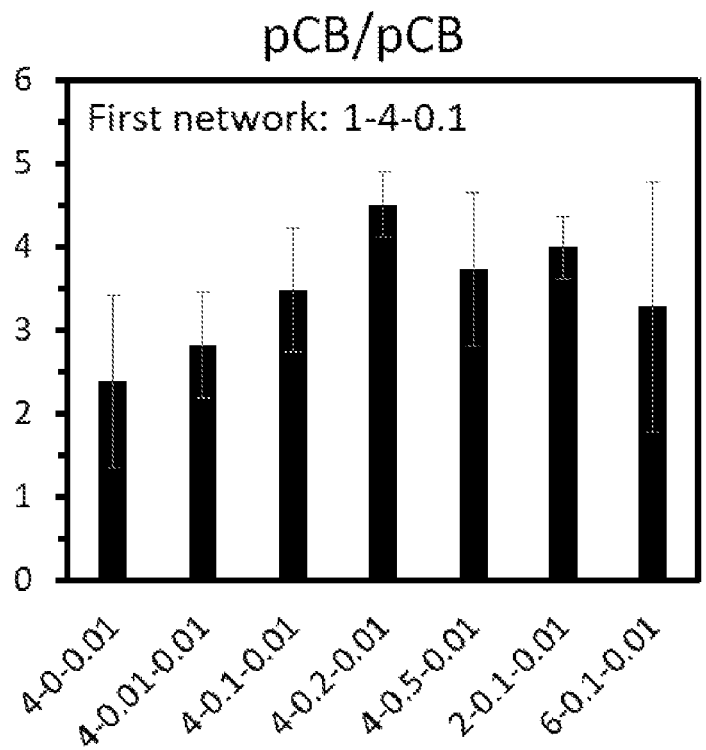
Figure 13C:
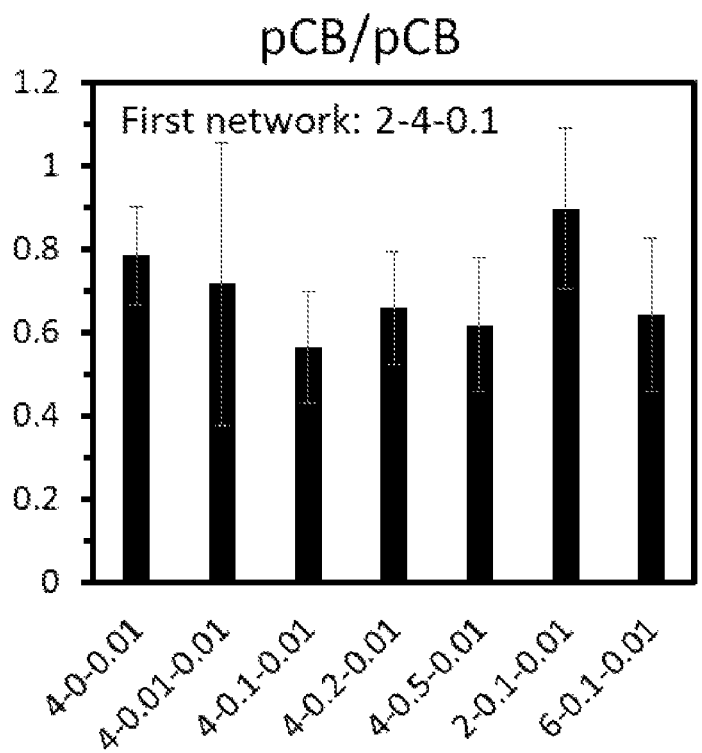
Figure 14A:
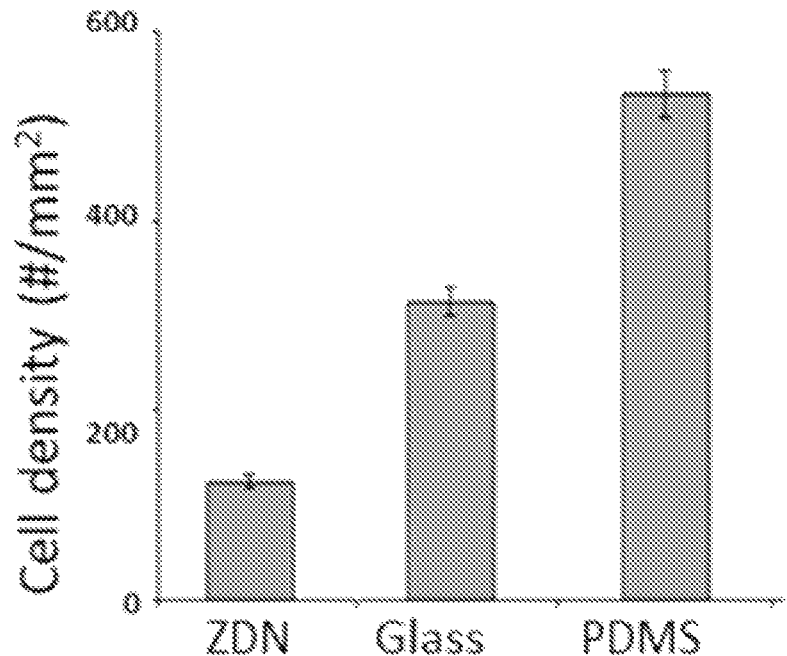
FIGS. 14A-14C compare attachment and adhesion tests of diatoms on a representative pCB/pSB ZDN hydrogel (1-4-0.1/4-0.1-0.01), glass, and PDMS: density (number/mm$^2$) of attached diatoms after 2 hours followed by washing (14A); removal (%) of diatoms due to exposure to a shear stress of 26 Pa (14B); and density (number/mm$^2$) of diatoms remaining after washing and exposure to a shear stress of 26 Pa (14C). Each point is the mean from 90 counts on 3 replicate slides. Bars show 95% confidence limits derived from arc-sine transformed data.
Figure 14B:
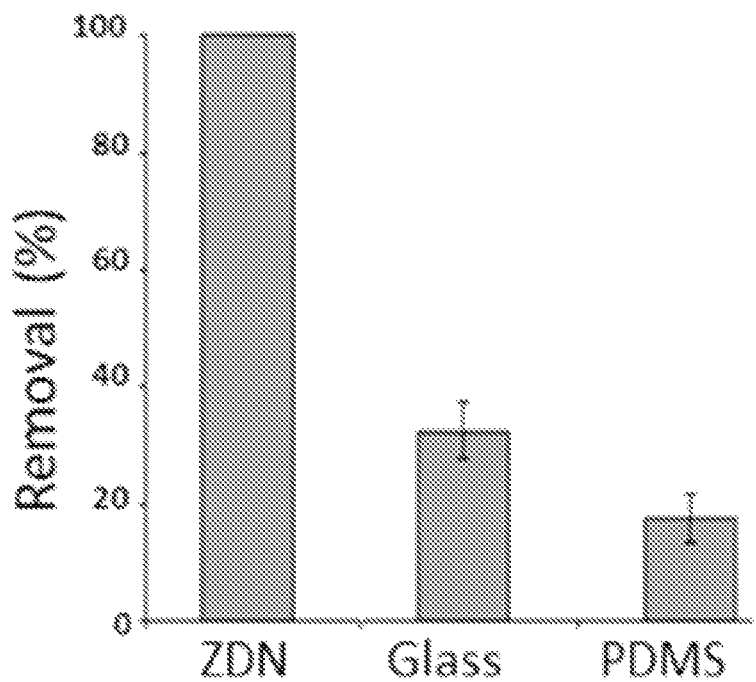
Figure 14C:
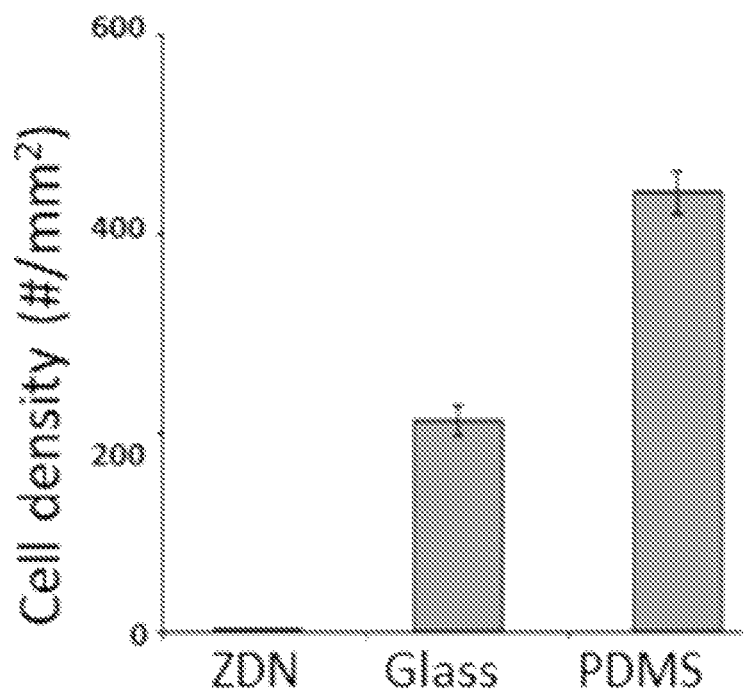
Figure 15A:
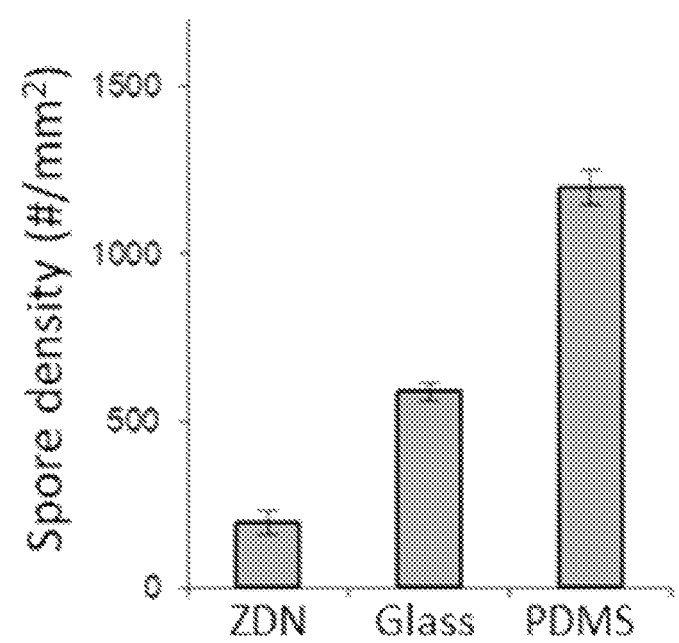
FIGS. 15A-15C compare attachment and adhesion tests of Ulva spores on a representative pCB/pSB ZDN hydrogel (1-4-0.1/4-0.1-0.01), glass, and PDMS: density (number/mm$^2$) of attached spores after 45 minutes settlement followed by washing (15A); removal (%) of spores due to washing and exposure to a shear stress of 52 Pa (15B); and density (number/mm$^2$) of spores remaining after washing and exposure to a shear stress of 52 Pa (15C). Each point is the mean from 90 counts on 3 replicate slides. Bars show 95% confidence limits derived from arc-sine transformed data.
Figure 15B:
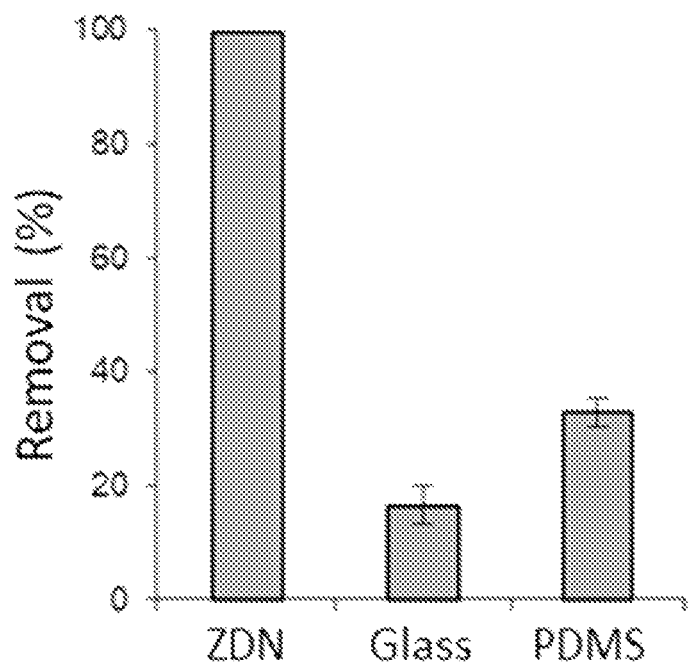
Figure 15C:
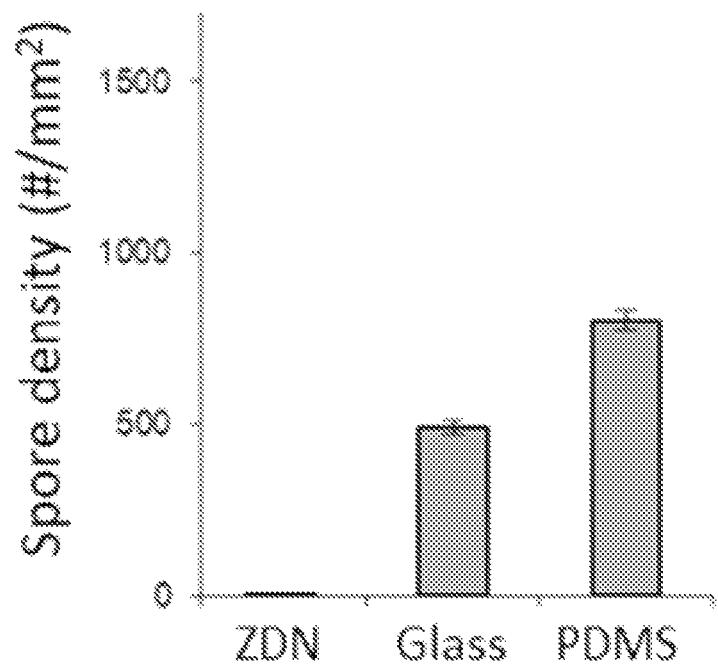
Figure 16:
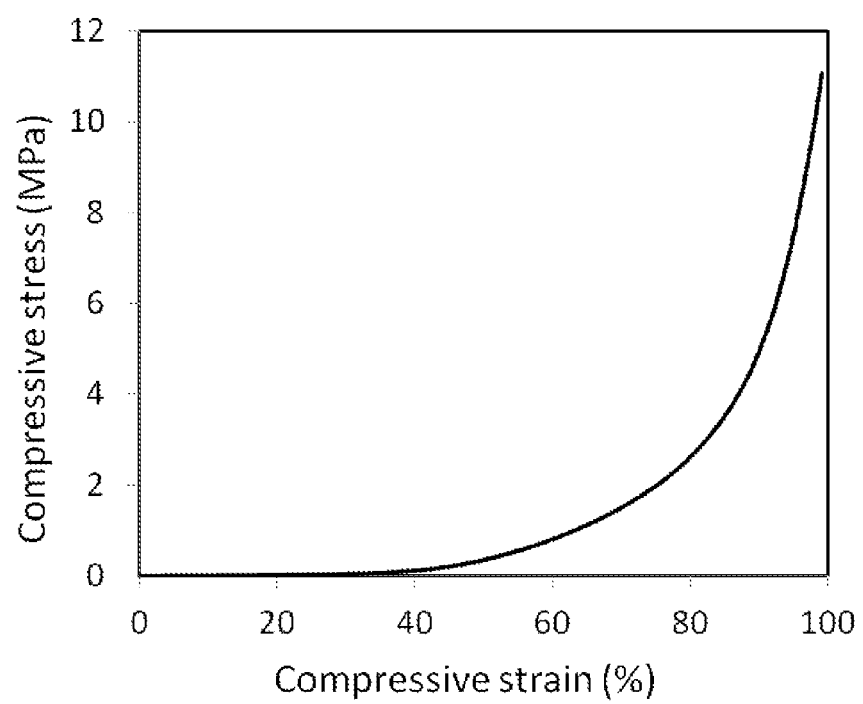
FIG. 16 compares compressive stress (MPa) and compressive strain (%) for a representative pTMAO/pSB ZDN hydrogel. The first network was made according to the composition 1-4-0.1 and the second network was made according the composition 4-0.1-0.01.

In general, for the zwitterionic double network hydrogels of the invention, the first network is relatively heavily crosslinked compared to the second network, which is relatively lightly crosslinked. In certain embodiments, the zwitterionic double network hydrogels of the invention can be defined as containing 2-15 mass % first network (e.g., pCB) and 85-98 mass % second network (e.g., pSB), as shown in FIG. 4 (given as mass %).

As described herein, the zwitterionic double network (ZDN) hydrogels of the invention are designated by the polymerization conditions for each of the first and second hydrogel networks: monomer molality-crosslinker mol %-initiator mol % (mol % based on polymerizable zwitterionic monomer or comonomers). For example, for a first network, a representative designation is 1-4-0.1; for a second network, a representative designation is 4-0.1-0.01; and for such a first and second network, the representative double network is designated 1-4-0.1/4-0.1-0.01.

As used herein, the term "monomer molality" refers to moles of monomer per kilogram of solvent of the solution used to prepare the first and second polymer networks.

As set forth above, for the zwitterionic double network hydrogels of the invention, the first network is relatively heavily crosslinked comparted to the second network, which is relatively lightly crosslinked. In a representative embodiment, the first network (1-4-0.1) has 4% crosslinker, which is considered to be a relatively high crosslinking density, to provide elasticity (or hardness), and the second network (4-0.1-0.01) has 0.1 mol % crosslinker, which is considered to be a relatively low crosslinking density, to provide viscosity (or softness). The combination of these two properties (elasticity/hardness and viscosity/softness) results in the high strength of the ZDN hydrogels of the invention.

Moreover, the second network provides a locking effect and is the majority of the ZDN hydrogel based on mass (amount to about 85 to 95 mol % of the whole ZDN hydrogel).

The following is a summary of monomer molality-crosslinker mol %-initiator mol % (mol % based on polymerizable zwitterionic monomer or comonomers) for representative ZDN hydrogels of the invention. In certain embodiments of the first network: [1-10]-[1-50]-[0.1-1]. In other embodiments of the first network: [1-2]-[2-4]-0.1. In one embodiment of the first network: 1-4-0.1. In certain embodiments of the second network: [1-10]-[0-10]-[0.01-1]. In other embodiments of the second network: [2-6]-[0-0.5]-0.01. In one embodiment of the second network: 4-0.1-0.01.

The following is a summary of monomer molality-crosslinker mol %-initiator mol % (mol % based on polymerizable zwitterionic monomer or comonomers) for representative ZDN hydrogels of the invention: first network poly (carboxybetaine), second network poly(sulfobetaine). In certain embodiments of the first network: [1-3]-[2-50]-[0.1-1]. In other embodiments of the first network: [1-2]-[2-4]-0.1. In one embodiment of the first network: 1-4-0.1. In certain embodiments of the second network: [2-10]-[0-0.5]-[0.01-1]. In other embodiments of the second network: [2-6]-[0-0.5]-0.01. In one embodiment of the second network: 4-0.1-0.01. For representative pCB/pSB ZDN hydrogels: [1-3]-[2-50]-[0.1-1]/[2-6]-[0-0.5]-[0.01-1]. For a representative pCB/pSB ZDN hydrogel: 1-4-0.1/4-0.1-0.01.

In certain embodiments of the ZDN hydrogels described herein, the first network has a ratio of [monomer molality]-[crosslinker mol %]-[initiator mol %], wherein mol % is based on polymerizable zwitterionic monomer or comonomers, of about [1-10]-[1-50]-[0.1-1]. In certain of these embodiments, the first network has a ratio of [monomer molality]-[crosslinker mol %]-[initiator mol %], wherein mol % is based on polymerizable zwitterionic monomer or comonomers, of about [1-2]-[2-4]-0.1.

In certain embodiments of the ZDN hydrogels described herein, the second network has a ratio of [monomer molality]-[crosslinker mol %]-[initiator mol %], wherein mol % is based on polymerizable zwitterionic monomer or comonomers, of about [1-10]-[0-10]-[0.01-1]. In certain of these embodiments, the second network has a ratio of [monomer molality]-[crosslinker mol %]-[initiator mol %], wherein mol % is based on polymerizable zwitterionic monomer or comonomers, of about [2-6]-[0-0.5]-0.01.

In certain embodiments of the ZDN hydrogels described herein, the first network is a poly(carboxybetaine) network having a ratio of [monomer molality]-[crosslinker mol %]-[initiator mol %], wherein mol % is based on polymerizable zwitterionic monomer or comonomers, of about [1-2]-[2-4]-[0.1]. In certain of these embodiments, the first network is a poly(carboxybetaine) network having a ratio of [monomer molality]-[crosslinker mol %]-[initiator mol %], wherein mol % is based on polymerizable zwitterionic monomer or comonomers, of about 1-4-0.1.

In certain embodiments of the ZDN hydrogels described herein, the second network is a poly(sulfobetaine) network having a ratio of [monomer molality]-[crosslinker mol %]-[initiator mol %], wherein mol % is based on polymerizable zwitterionic monomer or comonomers, of about [2-6]-[0-0.5]-[0.01-1]. In certain of these embodiments, the second network is a poly(sulfobetaine) network having a ratio of [monomer molality]-[crosslinker mol %]-[initiator mol %], wherein mol % is based on polymerizable zwitterionic monomer or comonomers, of about 4-0.1-0.01.

In certain embodiments of the ZDN hydrogels described herein, the first network is a poly(carboxybetaine) network having a ratio of [monomer molality]-[crosslinker mol %]-[initiator mol %], wherein mol % is based on polymerizable zwitterionic monomer or comonomers, of about [1-3]-[2-50]-[0.1-1], and the second network is a poly(sulfobetaine) network having a ratio of [monomer molality]-[crosslinker mol %]-[initiator mol %], wherein mol % is based on polymerizable zwitterionic monomer or comonomers, of about [2-6]-[0-0.5]-[0.01-1].

Methods for Making Zwitterionic Double Network Hydrogels

In certain embodiments, the zwitterionic double network hydrogels described herein can be obtained by a two-step process in which the first polymeric network is formed (e.g., by polymerization of zwitterionic monomers, crosslinking agents, and initiators, as necessary; copolymerization of zwitterionic and non-zwitterionic comonomers, crosslinking agents, and initiators, as necessary; or physical crosslinking of zwitterionic polymers or zwitterionic copolymers) and then soaked to equilibrium in a solution comprising precursors of the second polymeric network (e.g., zwitterionic monomers, crosslinking agents, and initiators, as necessary; zwitterionic and non-zwitterionic comonomers, crosslinking agents, and initiators, as necessary; or zwitterionic polymers or zwitterionic copolymers, and physical crosslinking agents), and the resulting first polymer network and the precursors of the second polymeric network are subject to polymerization conditions suitable to effect polymerization and formation of the second network and consequently the double network hydrogel.

In other embodiments, the zwitterionic double network hydrogels described herein can be obtained by a one-step (e.g., single pot) process, wherein the second polymeric network is formed in the presence of the first polymeric network. In the one-step (e.g., single pot) process, the second polymeric network is formed by (a) zwitterionic monomer polymerization (e.g., polymerization of monomer, crosslinking agent, and initiator), (b) zwitterionic and non-zwitterionic comonomer polymerization (e.g., copolymerization of comonomers, crosslinking agent, and initiator), or (c) physical crosslinking of a zwitterionic polymer or a zwitterionic copolymer (e.g., physical crosslinking of zwitterionic polymer or zwitterionic copolymer and physical crosslinking agent) in the presence of the first polymeric network.

Articles of Manufacture from Zwitterionic Double Network Hydrogels

In another aspect, the invention provides articles of manufacture comprising, in whole or in part, a zwitterionic double network hydrogel described herein.

In one embodiment, the article is a biomedical device. Representative biomedical devices include catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

In another embodiment, the article is a consumer product. Representative consumer products include wound dressings or wound care devices, skin sealants, dermatology devices (skin repair devices, bandages), cosmetic devices or formulations (topical creams, topical masks, injectable or implantable gels or other formulation for aesthetic, reconstructive or rejuvenation purposes), contact lens, OB/Gyn devices (implantable or topical birth control devices, vaginal slings), intra-ocular lens, aesthetic implants (breast implants, nasal implants, cheek implants), hormone control implants (blood sugar sensors, insulin pumps), urology devices (catheters, artificial urethrae).

In a further embodiment, the article is a marine product. Representative marine products include, in whole or in part, marine vessel hulls, marine structures, bridges, propellers, heat exchangers, periscopes, sensors, fish nets, cables, tubes/pipes, containers, membranes, and oil booms.

In another embodiment, the invention provides a microgel, comprising a zwitterionic double network hydrogel described herein.

In a further embodiment, the invention provides a surface coating for a substrate, comprising a zwitterionic double network hydrogel described herein. All or part of a surface of the substrate may be coated with the zwitterionic double network hydrogel.

In one embodiment, the substrate is a biomedical device. Representative biomedical devices include those listed above.

In another embodiment, the substrate is a consumer product. Representative consumer products include those listed above.

In a further embodiment, the substrate is a marine product. Representative marine products include those listed above.

As used herein, the term "about" refers to ±5% of the recited value.

The following examples are provided for the purpose of illustrating, not limiting, the invention.

EXAMPLES

Example 1

Preparation of Representative ZDN Hydrogels

In this example, the preparation of representative ZDN hydrogels of the invention is described.

Preparation of pCB/pSB ZDN hydrogels. ZDN hydrogels were synthesized by a two-step sequential free-radical polymerization. In the first step, the first network poly{3-[3-(acrylamidopropyl)dimethylammonio]propionate} (pCB) hydrogels were synthesized by photopolymerization using 1 m (molality) of CB, 4 mol % of crosslinker N,N-methylenebis(acrylamide) (MBAA), and 0.1 mol % of initiator 2-hydroxy-2-methylpropiophenone (1173) (both were relative to the CB monomer) in a transparent sheet molds or tubular rod molds under an ultraviolet (UV) irradiation with wavelength 305 nm and 6 watt power for 6 h in a nitrogen blanket. The polymerization condition of the first network hydrogel is denoted as 1-4-0.1 (CB molality-crosslinker mol %-initiator mol %). In the second step, the as-prepared pCB hydrogel was immersed into the precursor solution of second network containing 4 m of [2-(methacryloyloxy)ethyl]dimethyl-(3-sulfopropyl)ammonium hydroxide (SB), 0.1 mol % of MBAA and 0.01 mol % of initiator 1173 (both were relative to the SB monomer) for 24 h. The polymerization condition of the second network hydrogel is denoted as 4-0.1-0.01 (SB molality-crosslinker mol %-initiator mol %). Hence the polymerization condition of ZDN hydrogel is denoted as 1-4-0.1/4-0.1-0.01. The fully swollen first network hydrogel containing the precursor solution of second network is further polymerized by UV irradiation with wavelength 305 nm and 6 watt power for 6 h in a nitrogen blanket. After this two-step synthesis, the as-prepared pCB/pSB ZDN hydrogels were immersed in an aqueous solution for 1 day until they reached swelling equilibrium. In addition to 1-4-0.1/4-0.1-0.01, different combination of first network (1-2-0.1 and 2-4-0.1) and second network (4-0-0.01, 4-0.01-0.01, 4-0.2-0.01, 4-0.5-0.01, 2-0.1-0.01 and 6-0.1-0.01) were used for the synthesis of ZDN hydrogels.

Preparation of pCB/pCB, pCB/pSB, and pSB/pSB ZDN hydrogels. ZDN hydrogels were prepared according to the methods described above. In addition to 1-4-0.1/4-0.1-0.01, different combination of first network (1-2-0.1 and 2-4-0.1) and second network (4-0-0.01, 4-0.01-0.01, 4-0.2-0.01, 4-0.5-0.01, 2-0.1-0.01 and 6-0.1-0.01) were used for the synthesis of ZDN hydrogels.

Example 2

Equilibrium Swelling Ratio, Equilibrium Water Content, and Mass Percentage Tests In this example, equilibrium swelling ratio, equilibrium water content, and mass percentage tests used to measure the properties of a representative zwitterionic double network (ZDN) hydrogel of the invention, pCB/pSB ZDN hydrogel, are described.

The equilibrium swelling ratio (ESR) of equilibrated ZDN hydrogels to their as-prepared state was evaluated via a dimension measurement method. The as-prepared ZDN hydrogel disks were cut by a biopsy punch (5 or 10 mm in diameter). The diameters (r1) and heights (h1) of as-prepared ZDN hydrogel disks were measured and then soaked in deionized water at 37° C. for 2 days for completely swelling. The diameters (r2) and heights (h2) of their corresponding equilibrated state were measured. The ESRs were calculated as below. Each measurement was performed in triplicate.

$$ESR = \frac{r_2^2 \times h_2}{r_1^2 \times h_1} \times 100\%$$

The equilibrium water content (EWC) of ZDN hydrogels was measured through a gravimetric method. ZDN hydrogel disks (10 mm in diameter and 1 mm in thickness) were allowed to swell in deionized water until reaching equilibrium at 37° C. The equilibrated samples were taken out and their wet mass ($M_w$) were measured after the removal of excess water on the surface by rolling them on filter papers. The samples were then snap-frozen in liquid nitrogen and lyophilized for 2 days until a complete dryness and their dry mass ($M_d$) were measured. The EWCs were calculated as below. Each measurement was performed in triplicate.

$$EWC = \frac{M_w - M_d}{M_w} \times 100\%$$

The first network hydrogel were allowed to swell in deionized water until reaching equilibrium at 37° C. Their dry mass (MO were acquired after snap-frozen in liquid nitrogen and lyophilized for 2 days. The mass percentages (MS) of first network hydrogel were calculated as below. Each measurement was performed in triplicate.

$$MS = \frac{M_1}{M_d} \times 100\%$$

Example 3

Compression and Tensile Tests

In this example, compression and tensile tests used to measure the properties of a representative zwitterionic double network (ZDN) hydrogel of the invention, pCB/pSB ZDN hydrogel, are described.

Compressive and tensile tests were performed by a tensile-compressive mechanical tester (Instron 5543A, Instron Corp., Norwood, MA) with a 1 kN load cell to record the mechanical properties of the equilibrated pCB/pSB ZDN hydrogel samples. For tensile tests, crosshead speed was set at 10 mm min$^{-1}$. The equilibrium sheet samples were cut into rectangular pieces with dimensions of 20 mm×2 mm×0.50 mm. For compressive tests, the crosshead speed was set at 1 mm min$^{-1}$. The equilibrium tubular rod samples were cut with diameter and height of 5 and 3.5 to 4 mm, respectively. Average data were acquired by testing five specimens for each sample. The equilibrated pCB/pSB ZDN hydrogel had compressive fracture stress more than 15 MPa and stayed intact with 99% of compressive strain measured by compression test. The equilibrated pCB/pSB ZDN hydrogel had tensile fracture stress about 1 MPa and tensile fracture strain more than 300% measured by tensile test.

Example 4

Fibrinogen Adsorption Test

In this example, a fibrinogen adsorption test used to measure the properties of a representative zwitterionic double network (ZDN) hydrogel of the invention, pCB/pSB ZDN hydrogel (1-4-0.1/4-0.1-0.01), is described.

Fibrinogen (Fg) was chosen as the test protein to examine the nonfouling property of the ZDN samples. To measure Fg adhesion, the equilibrated pCB/pSB ZDN hydrogel samples were first incubated with 1 mL of 1 mg mL$^{-1}$ Fg in 0.15 M phosphate buffered saline (PBS) buffer at pH 7.4 for 1.5 hours, followed by 5 washes with pure PBS buffer. Samples were then transferred to new wells and incubated with 1 mL of horseradish peroxidase (HRP) conjugated anti-fibrinogen (1 µg mL$^{-1}$) in PBS buffer for 1.5 hours. All samples were then transferred to new wells after another 5 washes with pure PBS buffer. Next, 1 mL of 1 mg mL$^{-1}$ o-phenylenediamine (OPD) 0.1 M citrate phosphate pH 5.0 solution, containing 0.03% hydrogen peroxide was added. After 15 min incubation, the enzymatic reaction was stopped by adding an equal volume of 1N HCl. Absorbance value at 492 nm was recorded by a plate reader (Cytation 3, BioTek, Winooski, VT), and was normalized to that of tissue culture polystyrene (TCPS) sample. Average data were acquired from three specimens. The equilibrated pCB/pSB ZDN hydrogel sample were tested to have a fibrinogen binding level of less than 10% relative to that of TCPS.

Example 5

Serum Adsorption Test by Micro-BCA Assay

In this example, a serum adsorption test by micro-BCA assay used to measure the properties of a representative zwitterionic double network (ZDN) hydrogel of the invention, pCB/pSB ZDN hydrogel (1-4-0.1/4-0.1-0.01), is described.

Human serum fouling of the ZDN hydrogels was evaluated via a micro-BCA method. Pre-equilibrated ZDN hydrogel disks in PBS (5 mm in diameter and 1 mm in thickness) were suspended into 400 µL of undiluted human pooled serum in 24-well TCPS followed by incubation at 37° C. for 2 h. Before being transferred into new wells, all the samples were rinsed with 1 mL of PBS five times to remove the dissociative proteins. A micro-BCA assay was then directly carried out to determine the amount of proteins adsorbed on the hydrogel and the absorbance values at 562 nm of all the samples were recorded by a plate reader and were normalized to that of TCPS (96-well, control). Each sample was measured in triplicate.

Example 6

Platelet Attachment Analysis by Lactate Dehydrogenase Assay

In this example, a platelet attachment analysis by lactate dehydrogenase assay used to measure the properties of a representative zwitterionic double network (ZDN) hydrogel of the invention, pCB/pSB ZDN hydrogel (1-4-0.1/4-0.1-0.01), is described.

Platelets used for adhesion analysis were freshly collected from the blood of Sprague Dawley (SD) rats. Fresh blood collected was then immediately centrifuged at 200 g for 10 min to get platelet rich plasma (PRP). The residue was further centrifuged at 2000 g for 20 min to obtain platelet poor plasma (PPP). PRP and PPP were gently remixed and the final platelet density was adjusted to 2×108 mL$^{-1}$. Pre-equilibrated hydrogel disks in PBS (5 mm in diameter and 1 mm in thickness) were placed in 24-well TCPS with one disk per well, immersed with 400 µL of final platelet solution and incubated at 37° C. for 3 h. After incubation, the disks were rinsed with 1 mL of PBS five times and then transferred into new wells. The number of adhered platelets was determined by the lactate dehydrogenase (LDH) assay. For LDH assay, the rinsed samples were soaked in 24-well TCPS with 300 µL PBS and 10 µL 10× lysis buffer and incubated at 37° C., 5% carbon dioxide for 45 minutes. 50 µL reaction mixtures were then added into each well and incubated at room temperature for 30 minutes in the dark. To stop the reaction, 50 µL stop solution was added to each well and mixed by gentle pipetting. Finally 200 µL of the mixture was taken out from each well and the absorbance at 490 nm and 680 nm was measured by a platelet reader. The LDH activity was determined by subtracting the absorbance value of 680 nm from that of the 490 nm. Data were normalized to that of TCPS (96-well, control). Each sample was measured in triplicate.

Example 7

Cell Attachment Assay

In this example, a cell attachment assay used to measure the properties of a representative zwitterionic double network (ZDN) hydrogel of the invention, pCB/pSB ZDN hydrogel (1-4-0.1/4-0.1-0.01), is described.

Rat pancreatic β cells RIN-m5F and murine DC 2.4 dendritic cells were selected for the cell adhesion assay of the hydrogels. In brief, PBS pre-equilibrated and UV sterilized hydrogels disks (5 mm in diameter and 1 mm in thickness) were placed individually into the wells of a 96-well plate. RIN-m5F or DC 2.4 cells suspended in corresponding culture medium were seeded onto the hydrogels at a density of 1×105 cells/mL or 5×104 cells/mL, respectively, and allowed to grow for 24 h at 37° C. in a humidified atmosphere with 5% carbon dioxide. The medium was then removed and the hydrogels were gently washed with PBS and re-immersed with PBS. For optical imaging, cells adhesion and cellular morphology on the samples were observed at 400× magnification using a microscope (Nikon Eclipse 80i). For quantitative analysis of adhered cells, the samples were gently transferred to new wells and then the LDH assay was carried out following the protocol as described above. All the data were normalized to that of TCPS (96-well, control). Each sample was measured in sextuplicate.

Example 8

Sterilizing Representative pCB/pSB ZDN Hydrogel by Autoclaving

In this example, pCB/pSB ZDN hydrogels (1-4-0.1/4-0.1-0.01) were sterilized via a standard autoclaving method.

As-prepared pCB/pSB ZDN hydrogels were soaked in water or PBS until equilibrium and then sterilized at 121° C. for 30 min together with corresponding soaking solutions. The sterilized hydrogels were then cooled to room temperature for further use or test. Hydrogels experienced one, two, or three rounds of such heating-cooling autoclaving sterilization process were named as ZDN-R1, ZDN-R2 and ZDN-R3, respectively. The subsequent mechanical property, protein adhesion and cell adhesion tests of autoclaved ZDN hydrogels all followed the protocols described as above.

Example 9

In Vivo Implantation of Representative pCB/pSB ZDN Hydrogel Sheets

In this example, in vivo implantation of representative pCB/pSB ZDN hydrogel (1-4-0.1/4-0.1-0.01) sheets is described.

Six to eight-week-old male C57BL/6 mice were purchased from Charles River Labs. All the animal experiments were operated according to the federal guidelines and were approved by the University of Washington Animal Care and Use Committee. Subcutaneous implantation experiments were carried out to evaluate the foreign-body reaction and fibrous capsule formation of pCB/pSB ZDN hydrogels. Square pCB/pSB ZDN hydrogel disks (10 mm×10 mm×1 mm) were sterilized by autoclaving prior to implantation to prevent bacterial infection. pHEMA hydrogels with the same shape and dimension were set as positive control and were sterilized with UV for 30 min before surgery. The animal surgery was performed under anesthesia and aseptic conditions. In brief, each mouse was subcutaneously implanted with two ZDN or two pHEMA hydrogels symmetrically on the back with one sample on each side. Mice were anesthetized using 3% isoflurane and shaved. The area where the incision would be made was sterilized using iodine and 70% ethanol. A longitudinal incision (no longer than 1 cm) was made on the central dorsal surface using surgical scissors to provide access to the subcutaneous space. Subcutaneous pockets on either side of the incision were created with a blunt forceps for the implantation of the hydrogel samples. After implantation, the incisions were closed using wound nylon sutures and analgesic (Meloxicam) was administered. Twelve replicates of each type of hydrogel were implanted into six different mice to provide statistical significance in the histological studies. Mice were monitored until recovery from anesthesia and housed for 1 week, 4 weeks, 12 weeks, or 24 weeks before retrieving samples.

Example 10

Preparation of Representative ZDN Microgels

In this example, the preparation representative zwitterionic double network (ZDN) microgels of the invention, pCB/pSB ZDN hydrogel (1-4-0.1/4-0.1-0.01), is described.

ZDN microgels were produced using a stainless-steel piston and cylinder apparatus, where bulk hydrogels of the invention, pCB/pSB ZDN hydrogels (1-4-0.1/4-0.1-0.01), were extruded through progressively finer micronic steel meshes (TWP; 500 μm down to 25 μm pores). Microgels were passed through the final mesh size five times for size homogeneity.

Example 11

Ulva Spore Attachment and Adhesion Tests

In this example, ulva spore attachment and adhesion tests used to measure the properties of a representative representative zwitterionic double network (ZDN) hydrogel of the invention, pCB/pSB ZDN hydrogel (1-4-0.1/4-0.1-0.01) is described.

Attachment of spores. Zoospores were obtained from mature plants of $U.$ $linza$ by the standard method. A suspension of zoospores (15 ml; $7.5 \times 10^5$ spores ml$^{-1}$) was added to individual compartments of quadriPERM dishes containing the samples. After 45 minutes in darkness at about 20° C., the slides were observed under the microscope to determine whether there was any settlement on the surfaces. The samples were then washed by moving back and forth under seawater to remove unsettled (i.e., swimming) spores. Care was taken that the samples did not move through the air water interface. The samples were again viewed through the microscope and counts of spores were made on the wet samples. The density of zoospores attached to the surfaces was counted on each of 3 replicate slides using an image analysis system attached to a fluorescence microscope. Spores were visualised by autofluorescence of chlorophyll. Counts were made for 30 fields of view (each 0.15 mm$^2$) on each slide.

Strength of attachment of spores. After counting in the wet state, the spores attached to the coatings were 3 hours old (compared to 45 minutes in a standard assay). The slides, with attached spores, were exposed to a shear stress of 52 Pa in a specially designed turbulent flow water channel. Slides were then recounted in the wet state as described above.

Example 12

$N.$ $incerta$ Diatom Attachment and Adhesion Tests

In this example, $N.$ $incerta$ diatom attachment and adhesion tests used to measure the properties of a representative zwitterionic double network (ZDN) hydrogel of the invention, pCB/pSB ZDN hydrogel (1-4-0.1/4-0.1-0.01), is described.

Attachment of diatom. Cells of *N. incerta* were cultured in F/2 medium contained in 250 ml conical flasks. After 3 days the cells were in log phase growth. Cells were washed 3 times in fresh medium before harvesting and diluted to give a suspension with a chlorophyll a content of approximately 0.2 μg ml$^{-1}$. Cells were settled on three replicate coated slides of each sample, in individual quadriPERM® dishes containing 15 ml of suspension, at about 20° C. on the laboratory bench. After 2 hours the slides were exposed to 5 minutes of shaking on an orbital shaker (60 rpm) followed by a submerged wash in seawater to remove cells that had not attached (the immersion process avoided passing the samples through the air-water interface). Three slides of each type were counted, whilst still wet, using an image analysis system attached to a fluorescence microscope. Cells were visualised by autofluorescence of chlorophyll. Counts were made for 30 fields of view (each 0.56 mm$^2$) on each slide.

Strength of attachment of diatom. After counting, the slides with attached cells were exposed to a shear stress of 26 Pa in a water channel for 5 minutes. The number of cells remaining attached was counted wet as described above.

Example 13

Preparation of Representative pCB/pSB ZDN Hydrogel Coating

In this example, the single-pot method for preparing a representative zwitterionic double network (ZDN) hydrogel coating of the invention, pCB/pSB ZDN hydrogel (1-4-0.1/4-0.1-0.01) coating, is described.

The single-pot procedure was conducted by simply mixing zwitterionic pCB polymers, $Ca^{2+}$ ions, SB monomer, MBAA crosslinker, 1173 photo-reactive initiator and DI water in single container. The pCB interacted with $Ca^{2+}$ ions (ionic bonding) and formed the first network, followed by photo-initiating polymerization of SB via exposing to UV with wavelength 305 nm and 6 watt power for 6 h in a nitrogen blanket. The as-prepared ZDN hydrogel was immersed in DI water and the swelling ratio $V_{2e}/V_2$ is less than 2, where $V_2$ is the volume of ZDN hydrogel in the as-prepared state and $V_{ee}$ is the volume of ZDN hydrogel soaked in DI water until equilibrium.

The hybrid (physically and chemically) crosslinked pCB/pSB ZDN hydrogel was successfully formed via single-pot method. In addition to $Ca^{2+}$, $Mg^{2+}$, $Cu^{2+}$, and $Fe^{3+}$, were used respectively to interact with pCB to successfully form the first network via the ionic bonding.

Example 14

Preparation and Characteristics of Representative pTMAO/pSB ZDN Hydrogels

In this example, the preparation and characteristics of representative zwitterionic double network (ZDN) hydrogels of the invention, pTMAO/pSB ZDN hydrogels, are described.

pTMAO/pSB ZDN hydrogels were synthesized by a two-step sequential free-radical polymerization. In the first step, the first network poly(trimethylamine-N-oxide) (pTMAO) hydrogels were synthesized by photo polymerization using 1 m of TMAO, 4 mol % of cross-linker N,N-methylenebis(acrylamide) (MBAA), and 0.1 mol % of initiator 2-hydroxy-2-methylpropiophenone (1173) (both were relative to the TMAO monomer) in a transparent sheet molds or tubular rod molds under an ultraviolet (UV) irradiation with wavelength 305 nm and 6 watt power for 6 h in a nitrogen blanket. In the second step, the as-prepared pTMAO hydrogel was immersed into the precursor solution of second network containing 4 m of [2-(methacryloyloxy)ethyl]dimethyl-(3-sulfopropyl)ammonium hydroxide (SB), 0.1 mol % of MBAA and 0.01 mol % of initiator 1173 (both were relative to the SB monomer) for 2 days. The fully swollen first network hydrogel containing the precursor solution of second network is further polymerized by UV irradiation with wavelength 305 nm and 6 watt power for 6 h in a nitrogen blanket. After this two-step synthesis, the as-prepared pTMAO/pSB ZDN hydrogels were immersed in an aqueous solution for 1 day until they reached swelling equilibrium. The equilibrated pTMAO/pSB ZDN hydrogel had low swelling behavior in DI water with only 7% volume increase compared to that of the pTMAO/pSB ZDN hydrogel in the as-prepared state.

Compressive and tensile tests were performed by a tensile-compressive mechanical tester (Instron 5543A, Instron Corp., Norwood, MA) with a 10 kN load cell to record the mechanical properties of the equilibrated pTMAO/pSB ZDN hydrogel samples. For tensile tests, crosshead speed was set at 10 mm min$^{-1}$. The equilibrium sheet samples were cut into rectangular pieces with dimensions of 20 mm×2 mm×0.50 mm. For compressive tests, the crosshead speed was set at 1 mm min$^{-1}$. The equilibrium tubular rod samples were cut with diameter and height of 5 and 3.5 to 4 mm respectively. Average data were acquired by testing five specimens for each sample. The equilibrated pTMAO/pSB ZDN hydrogel had compressive fracture stress more than 10 MPa and stayed intact with 95% of compressive strain measured by compression test.

While illustrative embodiments have been illustrated and described, it will be appreciated that various changes can be made therein without departing from the spirit and scope of the invention.

The embodiments of the invention in which an exclusive property or privilege is claimed are defined as follows:

1. A double network hydrogel, comprising:
   (a) a first polymeric network comprising a first crosslinked zwitterionic polymer having from about 50 to about 100 mole percent zwitterionic moieties; and
   (b) a second polymeric network comprising a second crosslinked zwitterionic polymer having from about 50 to about 100 mole percent zwitterionic moieties,
   wherein the double network hydrogel has a compressive fracture stress of greater than about 0.9 MPa.

2. A double network hydrogel, comprising:
   (a) a first polymeric network comprising a first chemically crosslinked zwitterionic polymer having from about 50 to about 100 mole percent zwitterionic moieties; and
   (b) a second polymeric network comprising a second chemically crosslinked zwitterionic polymer having from about 50 to about 100 mole percent zwitterionic moieties.

3. The double network hydrogel of claim 1, wherein the first crosslinked zwitterionic polymer is a poly(carboxybetaine), poly(sulfobetaine), poly(sulfabetaine), poly(phosphobetaine), poly(phosphorylcholine), poly(choline phosphate), poly(trimethylamine-N-oxide), or a latent derivative thereof.

4. The double network hydrogel of claim 1, wherein the second crosslinked zwitterionic polymer is a poly(carboxybetaine), poly(sulfobetaine), poly(sulfabetaine), poly(phosphobetaine), poly(phosphorylcholine), poly(choline phosphate), poly(trimethylamine-N-oxide), or a latent derivative thereof.

5. The double network hydrogel of claim 1, wherein the first crosslinked zwitterionic polymer is a poly(carboxybetaine) and the second crosslinked zwitterionic polymer is a poly(sulfobetaine).

6. The double network hydrogel of claim 1, wherein the first crosslinked zwitterionic polymer is a poly(sulfobetaine) and the second crosslinked zwitterionic polymer is a poly(sulfobetaine).

7. The double network hydrogel of claim 1, wherein the first crosslinked zwitterionic polymer is a poly(trimethylamine-N-oxide) and the second crosslinked zwitterionic polymer is a poly(sulfobetaine).

8. The double network hydrogel of claim 1, wherein the first crosslinked zwitterionic polymer is a poly(phosphorylcholine) and the second crosslinked zwitterionic polymer is a poly(sulfobetaine).

9. The double network hydrogel of claim 1, wherein the second crosslinked zwitterionic polymer is a poly(sulfobetaine).

10. The double network hydrogel of claim 1 having a tensile fracture stress greater than about 0.3 MPa, a tensile fracture strain greater than about 200%, or a Young's modulus greater than about 0.01 MPa.

11. The double network hydrogel of claim 1, wherein the first polymeric network is chemically crosslinked or physically crosslinked, and the second polymeric network is chemically crosslinked or physically crosslinked.

12. The double network of claim 11, wherein physically crosslinked is crosslinking between polymers through ionic interaction, hydrogen bonding, or dipole-dipole interaction.

13. The double network hydrogel of claim 1 having a fibrinogen binding level of less than about 20% relative to that of tissue culture polystyrene tested via a fibrinogen binding assay in which a polymer surface is incubated at 37° C. for 90 minutes with a 1.0 mg/mL fibrinogen solution in 0.15 M phosphate buffered saline at pH 7.4.

14. The double network hydrogel of claim 1 obtained by a two-step process, wherein the first polymeric network is formed, and then the first polymeric network is soaked to equilibrium in a solution comprising precursors of the second polymeric network, followed by the polymerization of the precursors to provide the double network.

15. The double network hydrogel of claim 1 obtained by a single-pot process, wherein the second polymeric network is formed by (a) monomer polymerization, (b) comonomer copolymerization, or (c) physical crosslinking of a zwitterionic polymer or zwitterionic copolymer in the presence of the first polymeric network.

16. An article of manufacture comprising, in whole or in part, a double network hydrogel of claim 1.

17. A microgel, comprising a double network hydrogel of claim 1.

18. A surface coating for a substrate, comprising a double network hydrogel of claim 1.

19. The double network hydrogel of claim 2, wherein the first crosslinked zwitterionic polymer is a poly(carboxybetaine), poly(sulfobetaine), poly(sulfabetaine), poly(phosphobetaine), poly(phosphorylcholine), poly(choline phosphate), poly(trimethylamine-N-oxide), or a latent derivative thereof.

20. The double network hydrogel of claim 2, wherein the second crosslinked zwitterionic polymer is a poly(carboxybetaine), poly(sulfobetaine), poly(sulfabetaine), poly(phosphobetaine), poly(phosphorylcholine), poly(choline phosphate), poly(trimethylamine-N-oxide), or a latent derivative thereof.

21. The double network hydrogel of claim 2, wherein the first crosslinked zwitterionic polymer is a poly(carboxybetaine) and the second crosslinked zwitterionic polymer is a poly(sulfobetaine).

22. The double network hydrogel of claim 2, wherein the first crosslinked zwitterionic polymer is a poly(sulfobetaine) and the second crosslinked zwitterionic polymer is a poly(sulfobetaine).

23. The double network hydrogel of claim 2, wherein the first crosslinked zwitterionic polymer is a poly(trimethylamine-N-oxide) and the second crosslinked zwitterionic polymer is a poly(sulfobetaine).

24. The double network hydrogel of claim 2, wherein the first crosslinked zwitterionic polymer is a poly(phosphorylcholine) and the second crosslinked zwitterionic polymer is a poly(sulfobetaine).

25. The double network hydrogel of claim 2, wherein the second crosslinked zwitterionic polymer is a poly(sulfobetaine).

26. The double network hydrogel of claim 2 having a tensile fracture stress greater than about 0.3 MPa, a tensile fracture strain greater than about 200%, or a Young's modulus greater than about 0.01 MPa.

27. The double network hydrogel of claim 2 having a fibrinogen binding level of less than about 20% relative to that of tissue culture polystyrene tested via a fibrinogen binding assay in which a polymer surface is incubated at 37° C. for 90 minutes with a 1.0 mg/mL fibrinogen solution in 0.15 M phosphate buffered saline at pH 7.4.

28. The double network hydrogel of claim 2 obtained by a two-step process, wherein the first polymeric network is formed, and then the first polymeric network is soaked to equilibrium in a solution comprising precursors of the second polymeric network, followed by the polymerization of the precursors to provide the double network.

29. The double network hydrogel of claim 2 obtained by a single-pot process, wherein the second polymeric network is formed by (a) monomer polymerization, (b) comonomer copolymerization, or (c) physical crosslinking of a zwitterionic polymer or zwitterionic copolymer in the presence of the first polymeric network.

30. An article of manufacture comprising, in whole or in part, a double network hydrogel of claim 2.

31. A microgel, comprising a double network hydrogel of claim 2.

32. A surface coating for a substrate, comprising a double network hydrogel of claim 2.

33. The double network hydrogel of claim 1, wherein the first crosslinked zwitterionic polymer is a poly(carboxybetaine) and the second crosslinked zwitterionic polymer is a poly(sulfobetaine).

34. The double network hydrogel of claim 1, wherein the first crosslinked zwitterionic polymer is a poly(trimethylamine-N-oxide) and the second crosslinked zwitterionic polymer is a poly(sulfobetaine).

35. The double network hydrogel of claim 1, wherein the first crosslinked zwitterionic polymer is a poly(phosphorylcholine) and the second crosslinked zwitterionic polymer is a poly(sulfobetaine).

36. A microgel, comprising a double network hydrogel, the double network hydrogel comprising:
(a) a first polymeric network comprising a first crosslinked polymer, wherein the first polymeric network is a hydrogel; and (b) a second polymeric network comprising a second crosslinked zwitterionic polymer having from about 50 to about 100 mole percent zwitterionic moieties, wherein the double network hydrogel has a compressive fracture stress of greater than about 0.9 MPa; or (c) a first polymeric network comprising a first crosslinked polymer, wherein the first polymeric network is a hydrogel; and (d) a second polymeric network comprising a chemically crosslinked poly(sulfobetaine) having from about 50 to about 100 mole percent zwitterionic moieties.

37. A surface coating for a substrate, comprising a double network hydrogel, the double network hydrogel comprising:

(a) a first polymeric network comprising a first crosslinked polymer, wherein the first polymeric network is a hydrogel; and (b) a second polymeric network comprising a second crosslinked zwitterionic polymer having from about 50 to about 100 mole percent zwitterionic moieties, wherein the double network hydrogel has a compressive fracture stress of greater than about 0.9 MPa; or (c) a first polymeric network comprising a first crosslinked polymer, wherein the first polymeric network is a hydrogel; and (d) a second polymeric network comprising a chemically crosslinked poly(sulfobetaine) having from about 50 to about 100 mole percent zwitterionic moieties.

\* \* \* \* \*